(12) United States Patent
Kinoshita et al.

(10) Patent No.: US 8,231,908 B2
(45) Date of Patent: Jul. 31, 2012

(54) SHEET-LIKE COMPOSITION

(75) Inventors: Shigeru Kinoshita, Osaka (JP);
Takahiro Nakamura, Kyoto (JP);
Norihiko Yokoi, Kyoto (JP); Eiji Kurihara, Kobe (JP)

(73) Assignees: ArBlast Co., Ltd., Hyogo (JP); Shigeru Kinoshita, Osaka (JP)

( * ) Notice: Subject to any disclaimer, the term of this patent is extended or adjusted under 35 U.S.C. 154(b) by 760 days.

(21) Appl. No.: 11/989,296

(22) PCT Filed: Jul. 19, 2006

(86) PCT No.: PCT/JP2006/314245
§ 371 (c)(1),
(2), (4) Date: Feb. 2, 2009

(87) PCT Pub. No.: WO2007/013331
PCT Pub. Date: Feb. 1, 2007

(65) Prior Publication Data
US 2009/0175954 A1 Jul. 9, 2009

(30) Foreign Application Priority Data

Jul. 25, 2005 (JP) ................................. 2005-214339

(51) Int. Cl.
*A61K 35/54* (2006.01)
(52) U.S. Cl. ....................................................... 424/582
(58) Field of Classification Search .................. None
See application file for complete search history.

(56) References Cited

U.S. PATENT DOCUMENTS

2005/0084971 A1* 4/2005 Smeekens et al. ............ 435/468
2006/0228339 A1* 10/2006 Wang .......................... 424/93.7

FOREIGN PATENT DOCUMENTS

| JP | 05-056987 | 3/1993 |
| WO | WO 0108716 A1 * | 2/2001 |
| WO | WO-03/043542 | 5/2003 |
| WO | WO-03/092762 | 11/2003 |
| WO | WO-2004/078225 | 9/2004 |

OTHER PUBLICATIONS

Szurman et al, Sutureless amniotic membrane fixation with fibrin glue for ocular surface reconstruction, IOVS, (Apr. 2004) vol. 45, No. Suppl. 2, pp. U335. Meeting Info.: Annual Meeting of the Association-for-Research-in-Vision-and-Ophthalmology. Ft Lauderdale, FL, USA. Apr. 24-29, 2004. Assoc Res Vis & Ophthalmol.*
Chan et al, Advances in the use of adhesives in ophthalmology, Current Opinion in Ophthalmology, (Aug. 2004) vol. 15, No. 4, pp. 305-310.*
International Search Report dated Sep. 19, 2006, issued on PCT/JP2006/314245.

* cited by examiner

*Primary Examiner* — Qiuwen Mi
(74) *Attorney, Agent, or Firm* — Ann R. Pokalsky, Esq.; Dilworth & Barrese, LLP

(57) ABSTRACT

A sheet-shaped composition is provided which has an improved preservability and handling readiness, as well as a high flexibility in use. Amnion with trehalose added thereto is utilized. Addition of trehalose improves the flexibility of the amnion, and prevents basal membrane and stratum compactum from being damaged during lyophilization process.

24 Claims, 15 Drawing Sheets

|  | Main application site | Exemplary application method | Desired form of amnion | Main purpose |
|---|---|---|---|---|
| 1-1 | Abdominal and thoracic organ | Secure after coverage | Desiccation/cryopreservation | Reconstruction, antiadhesive |
| 1-2 | Immediately under wound | Indwell | Reinforced desiccation | Antiadhesive |
| 1-3 | Pelvic floor | Indwell | Reinforced desiccation | Antiadhesive |
| 1-4 | Peritoneal | Secure after coverage | Desiccation/cryopreservation | Reconstruction |
| 1-5 | Peritoneal and organ, etc. | Secure after coverage | Desiccation/cryopreservation | Reconstruction |
| 1-6 | Abdominal and thoracic organ | Secure after coverage | Desiccation/cryopreservation | Reconstruction, antiadhesive |
| 2-1 | Salpinx | Secure after coverage | Desiccation/cryopreservation | Antiadhesive |
| 2-2 | Pelvic floor | Indwell | Reinforced desiccation | Antiadhesive |
| 3-1 | Conjunctiva | Secure after coverage | Desiccation/cryopreservation | Antiadhesive |
| 3-2 | Sclera, eyelid | Secure after coverage | Desiccation/cryopreservation | Antiadhesive |
| 3-3 | Sclera | Secure after coverage | Desiccation | Antiadhesive |

FIG.1 a)
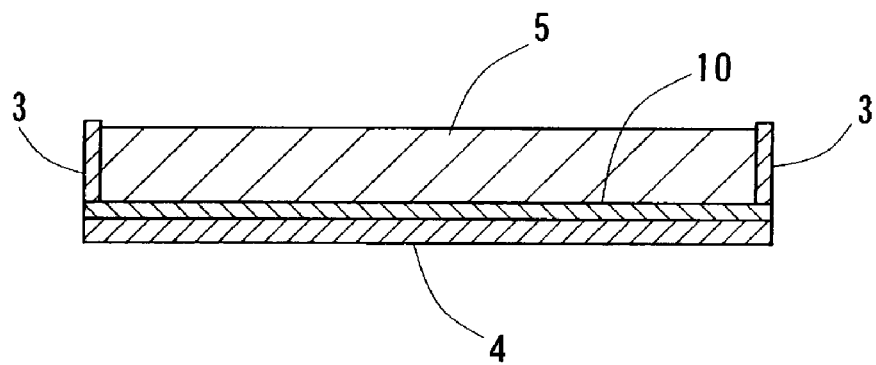
b)
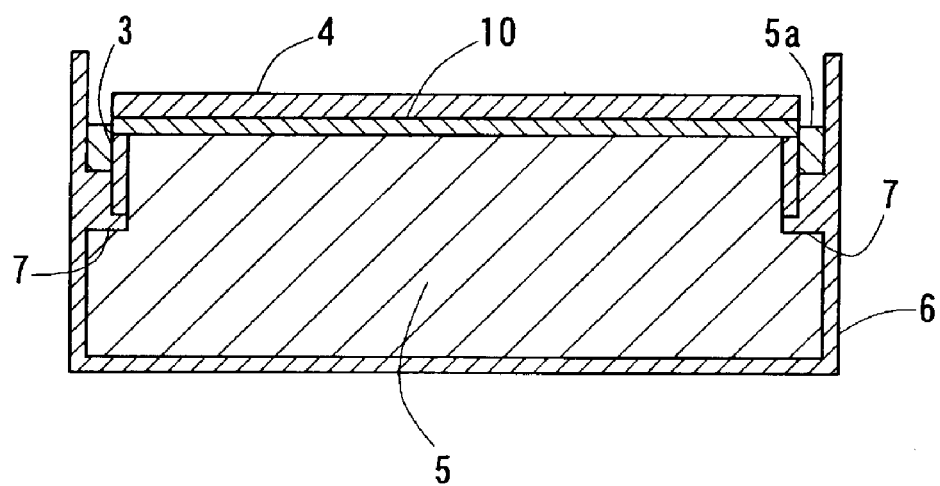
FIG.16

| | Raw amnion (with epithelium) | Manually treated amnion | Trypsin-treated amnion |
|---|---|---|---|
| Amniotic epithelial cells | + | — | — |
| Basal membrane components | | | |
| Collagen IV | + | + | + |
| Collagne VII | + | + | + |
| Laminin-5 | + | + | + |
| Stratum compactum components | | | |
| Collagen I | + | + | + |
| Collagen III | + | + | + |
| Collagen V | + | + | + |
| Fibronectin | + | + | ± |

SHEET-LIKE COMPOSITION

TECHNICAL FIELD

This invention relates to a sheet-shaped composition using an amnion and a method for producing the same. The sheet-shaped composition according to the invention is applicable as, for example, culture substrate for producing artificial tissues (such as corneal epithelium), transplant materials for reconstructing eye surfaces, skins, etc, and as antiadhesive materials.

BACKGROUND ART

Amnion has preferable properties as transplant materials, such as high biocompatibility and flexibility, and has found its use in reconstruction of corneal epithelium and other various tissues (See Patent Documents 1 through 4). Use of amnion can be largely classified into two groups. Namely, it can be applied directly for any injured area to reconstruct the tissues, or can be used as a culture substrate for culturing cells. Flexibility of amnion is a crucial property for any one of these applications. Because of its high flexibility, amnion can cover injured site without any gaps, with a favorable adhesion and take onto the injured site, resulting in a favorable therapeutic effect. On the other hand, when amnion is applied as a culture substrate for culturing cells, its high flexibility enables it to achieve a favorable cell amplification and normal organization (differentiation).

[Patent Document 1] Japanese Patent Publication No. 5-56987, the Gazette
[Patent Document 2] International Publication No. 03/043542, A1 Leaflet
[Patent Document 3] International Publication No. 03/92762, A1 Leaflet
[Patent Document 4] International Publication No. 2004/078225, A1 Leaflet

DISCLOSURE OF THE INVENTION

Problems to be Solved by the Invention

Amnion covers the outermost layer of uterine and placenta in mammals, and is derived during delivery. Accordingly, since fresh amnion cannot always be available, long-term preservation and readiness in handling of amnion have been in demand for clinical application. Thus, derived amnion has been stored in a desiccated state for enhanced preservation and handling readiness. The desiccation process, however, while providing a significantly enhanced preservability, greatly reduces the flexibility of the amnion after returning it back to a wet state due to denatured constituent proteins. Such a low flexibility may impair coverage of entire injured site, and lowers adhesiveness and take thereon. In addition, once desiccated, the amnion has a low cell proliferation rate thereon, and hampers the layering, thus causing no normal organization (differentiation). This may be due to drastically impaired flatness of the amnion surface accompanying the reduction of flexibility.

The present invention, seeking for the solution of the above problems, pursues to provide a sheet-shaped composition comprising amnion which has superior preservability and handling readiness, as well as flexibility in use.

Means to Solve the Problems

In order to achieve the above objective, the present inventors first tried modifying amnion to enhance the flexibility. As a result, if treated with trehalose, one of disaccharides, the amnion restored its flexibility when returned to its wet state, even if it had been desiccated. Moreover, it was found that the restored flexibility was at an equivalent level to that of untreated amnions (raw amnion). Thus, it was revealed that treatment with trehalose is effective in enhancing the flexibility of amnion.

Surprisingly, it was also shown that the treatment with trehalose had an additional effect of enhancing transparency of amnion. Thus, it was revealed that treatment of the amnion with trehalose is extremely effective when amnion is used for any application where as high a transparency as possible is required (such as in corneal reconstruction).

In addition, since treatment with trehalose increased tensile strength of the amnion and provided a tough amnion than raw ones, it was shown that treatment with trehalose is effective in enhancing the handling readiness and preservability after transplant of the amnion.

Furthermore, since the biocompatibility of the amnion treated with trehalose was determined to be as high as that of raw amnions, it was demonstrated that treatment with trehalose never adversely affects its biocompatibility.

With the knowledge thus accumulated, the effect of trehalose on the function of amniotic membrane as cell culture substrate was examined. Specifically, corneal epithelial cells were cultured on amnion that had been treated with trehalose, and the cell proliferation rates and layering thereon were determined. The results revealed a favorable cell proliferation and 5-7 layering, indicating a significant enhancement comparative to those layering (1-2 layering) on amnion that had not been treated with trehalose. Thus, it was shown that the treatment with trehalose is effective also in use of amnion as cell culture substrate.

Subsequently, a sheet of amnion with cell layers formed thereon was transplanted on eye surface of animals to determine the reconstruction effect. As a result, a favorable adhesion and take was revealed, with no deficient in reconstructing the eye surface but with a high transparency retained.

The present invention is mainly based on the above knowledge and provides a sheet-shaped composition as described below.

[1] A sheet-shaped composition comprising an amnion with trehalose added thereto.

[2] The sheet-shaped composition according to [1], in a frozen or desiccated state.

[3] The sheet-shaped composition according to [2], in a lyophilized state.

[4] The sheet-shaped composition according to [1] through [3], wherein the amnion is an amnion with epithelial cell layer removed.

[5] The sheet-shaped composition according to [1] through [4], wherein the amnion has basal membrane components Collagen IV, Collagen VII, and Laminin 5 that are detected at an equivalent intensity to that in untreated amnion.

[6] The sheet-shaped composition according to [1] through [5], wherein the amnion is a human amnion.

[7] The sheet-shaped composition according to [1] through [6], wherein cell layer consisting of tissue-derived cells is formed on the amnion.

[8] The sheet-shaped composition according to [7], wherein the tissue-derived cells are layered in the cell layer.

[9] The sheet-shaped composition according to [7], wherein the tissue-derived cells are derived from corneal epithelium, conjunctival epithelium, skin epidermis, follicular epithelium, oral mucosa epithelium, pigment epithelium iris, pigment epithelium retina, airway mucosa epithelium, or intestinal mucosa.

[10] The sheet-shaped composition according to [7], wherein the cell layer is composed of about 5-7 layered cells, and has properties similar to those of corneal epithelium.

[11] The sheet-shaped composition according to [1] through [6], for use as antiadhesive materials or reconstruction materials for surface tissues damaged during surgical invasion.

[12] The sheet-shaped composition according to [1] through [11], wherein the amnion has any adhesive component attached on its chorion side surface.

[13] The sheet-shaped composition according to [12], wherein the adhesive component is fibrinogen and thrombin.

[14] The sheet-shaped composition according to [12], wherein the adhesive component is fibrinogen, thrombin and aprotinin.

[15] The sheet-shaped composition according to [1] through [14], wherein the chorion side surface of the amnion is covered with bioabsorbable material.

In another embodiment, the present invention provides a transplantation method as follows.

[16] Transplant method using any one of sheet-shaped composition as implant material.

In another embodiment, the present invention provides a method for producing a sheet-shaped composition as follows.

[17] A method for producing a sheet-shaped composition, comprising the steps of:
 (a) preparing an amnion;
 (b) adding trehalose to said amnion.

[18] The method according to [17], further comprising the step of:
 (c) freezing or desiccating said amnion after step (b).

[19] The method according to [18], further comprising the step of:
 (d) sterilizing said amnion after step (c).

[20] The method according to any one of [17] through [19], wherein step (a) comprises the step of:
 (a1) removing epithelium from said amnion.

[21] The method according to [20], wherein step (a1) comprises the following steps of:
 (1) preparing an amnion separated from an organism,
 (2) freeze-thawing said amnion,
 (3) subjecting said amnion after freeze-thawing to tryptic treatment,
 (4) washing said amnion after tryptic treatment.

[22] The method according to [21], wherein the freezing temperature during said freeze-thawing is from about −20° C. to about −80° C., and the thawing temperature is from about 4° C. to about 50° C.

[23] The method according to [21] or [22], characterized by repetition of said freeze-thawing process twice or more times.

[24] The method according to any one of [20] through [23], characterized by the tryptic treatment being performed using a tryptic solution having a tryptic concentration of from about 0.01% (w/v) to about 0.05% (w/v).

[25] The method according to [24], characterized by the tryptic solution comprising from about 0.1 mM to about 0.6 mM of a chelator selected from the group consisting of EDTA, NTA, DTPA, HEDTA, GLDA, and any combination thereof.

[26] The method according to any one of [20] through [25], characterized by the tryptic treatment being performed under the condition such that the tryptic solution is contacted with only the epithelium side of said amnion.

[27] The method according to any one of [20] through [26], wherein the following step of;

(A) forming a cell layer consisting of tissue-derived cells on said amnion is performed prior to the step of (b).

BRIEF DESCRIPTION OF THE DRAWINGS

FIG. 1 is a table showing the applications (applied sites, exemplary application method, preferable form of the amnion, and main purpose) of the sheet-shaped composition as tissue-reconstructing material.

FIG. 16 is a pair of figures showing the procedure of tryptic treatment. In the figure (a), the amnion secured in a frame is immersed in tryptic solution with its epithelial side down. In the figure (b), trypsin is acted upon the epithelial side of the amnion by pouring tryptic solution into the frame.

Figure 2:
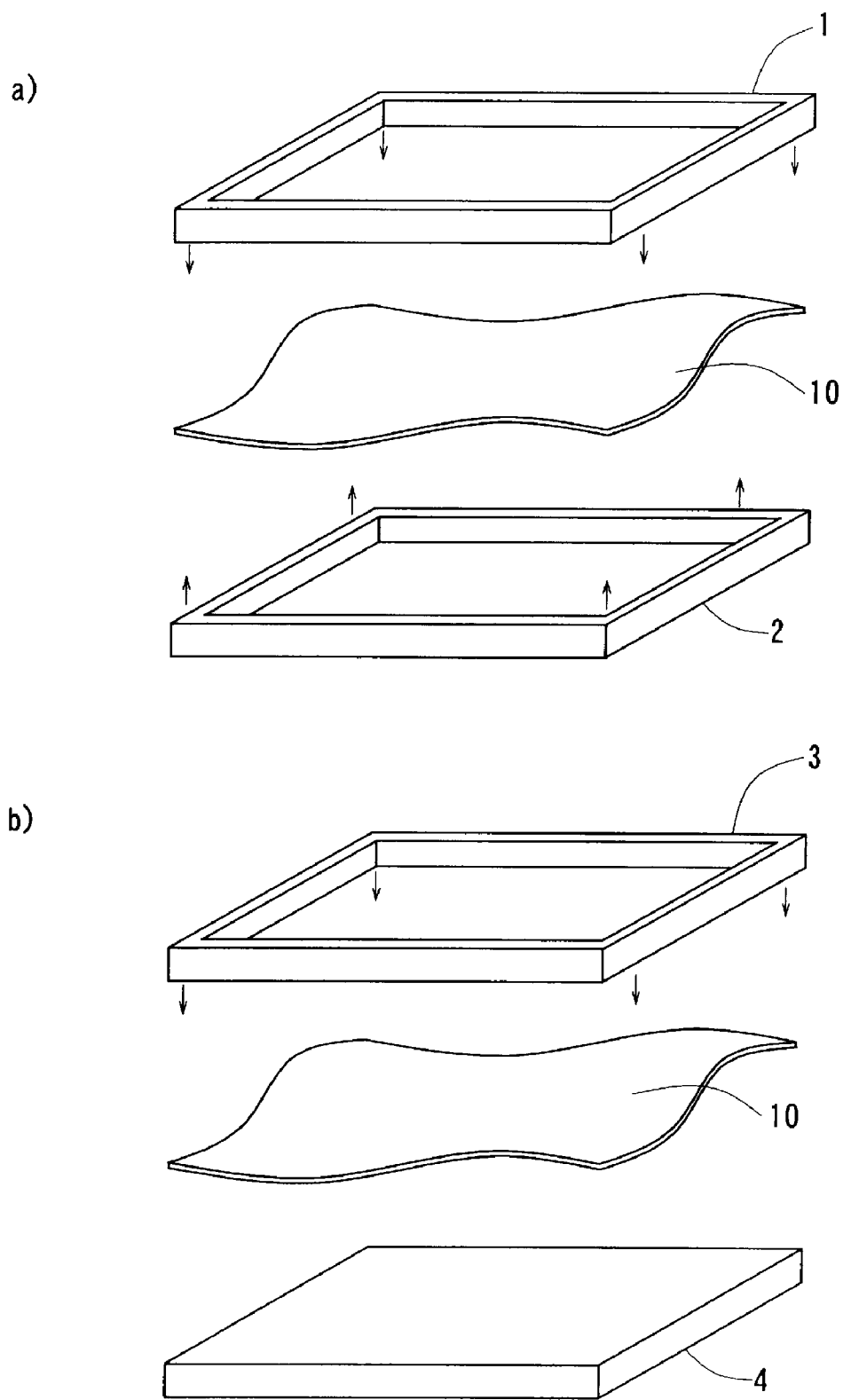
FIG. 2 is a series of graphs showing the procedure for securing amnions. The amnion in (a) is clamped between a pair of frame, and that in (b) is clamped between a frame and a plate-like member.

EXPLANATION OF THE NUMERALS 1, 2, 3 frame
4 plate-like member
5 tryptic solution
10 amnion
11 culture dish (culture dish)
12 culture insert (culture insert container)
13 amnion
14 corneal epithelial cells
15 3T3 cell layer
16 culture medium

THE BEST MODE OF CARRYING OUT THE INVENTION

In one embodiment, the present invention relates to a sheet-shaped composition. According to the invention, the sheet-shaped composition utilizes an amnion as its main component. Because of its high clarity and strength, amnion can form sheet-shaped composition with an improved clarity and strength. Moreover, a high biocompatibility and low immunogenicity of amnion lead to an improved biocompatibility and low immunogenicity of the resulting sheet-shaped composition. Use of amnion can be expected to exert various actions, such as anti-inflammatory action, suppression of scar formation, and inhibition of angiogenesis. Use of amnion is preferable also in respect of favorable formation of the cell layer, if contained in the sheet-shaped composition according to the invention. Specifically, as will be described later, if the sheet-shaped composition comprising the cell layer is formed by seeding and culturing a predetermined type of cells on an amnion which serves as substrate (support), such a use of amnion results in a favorable adhesion and proliferation of cells, as well as a formation of the cell layers since an amnion has a property of allowing a favorable adhesion and proliferation of cells thereon.

(Origin of Amnion)

"Amnion" is a membrane covering the outermost layer of uterine and placenta in mammals, and consists of an underlying collagen-rich parenchyma, basal membrane thereon and epithelial layer. Amnion of, for example, human, monkey, chimpanzee, swine, horse and bovine can be used. Amongst them, human amnion is preferably used because its safety is reliable, including its low immunogenicity and virus infection-probability.

[Addition of Trehalose]

The sheet-shaped composition according to the present invention utilizes an amnion with trehalose added thereto. The inventors have found that the addition of trehalose improves the flexibility of the amnion, especially when the amnion is lyophilized. In addition, as will be shown in the Embodiments described later, it was found that the amnion with trehalose added thereto serves favorably as a substrate for culturing cells. The sheet-shaped composition according to the invention that is constructed based on such knowledge has a high flexibility, and allows for favorable proliferation and layering of cells when used as a substrate for culturing cells.

One might focus on degradation of matrix proteins contained in an amnion, which leads to its lower strength, making the amnion more susceptible to damages. Moreover, the amnion that has its matrix protein degraded can no longer hold its moisture tight inside, become brittle and less resilient. The trehalose added to the amnion is expected to act upon the site of the matrix proteins where binding has loosened, thereby reinforcing the binding between proteins, normalizing the moisture capture inside the amnion, and maintaining the moisture, integrity and flexibility native to the amnion. Further, by adding trehalose, the matrix proteins contained in the amnion may be prevented from becoming soft during lyophilization process, and can effectively be protected from swelling and weakening in water.

Trehalose (material name, general name) is a compound the is represented by α-D-Glucopyranosyl (1,1)-α-D-Glucopyranoside.

Addition of trehalose to an amnion can be performed by, for example, treating the amnion with trehalose solution. Exemplary method of adding trehalose will be described later in detail.

In one embodiment of the invention, the composition consists essentially of an amnion with trehalose added thereto.

(State of the Amnion)

In one embodiment of the invention, an amnion having its epithelial cell layer removed is utilized. An amnion with its epithelial cell layer removed is extremely safer since it does not cause any immunological rejection or other problems arising against epithelial cells. In addition, since cell adhesion and proliferation that can take place on the amnion with its epithelium removed produce superior results, a quality cell sheet can be constructed in a shorter time period, thus providing an advantage in the manufacture of the sheet-shaped composition.

Absence of the epithelial layer on the amnion can be confirmed by determining an absence of any cells of the amniotic epithelial layer on the resultant sheet-shaped composition according to the invention.

On the other hand, an amnion with its epithelial layer retained can be utilized in constructing the sheet-shaped composition according to the invention. Retention of the epithelial layer on the amnion allows one to perform a thorough sterilization procedure such as γ-ray treatment, thereby ensuring the safety of the sheet-shaped composition.

(Use of Reconstructed Amnion)

A reconstructed amnion can be used to construct the sheet-shaped composition according to the invention. Specifically, an amnion can be subjected to homogenizer, ultrasound, enzymatic or other treatment to decompose it, and then reconstructed into a membrane-like form. Treatment may be preferably performed using a homogenizer since it is expected to relatively highly retain a structure having a minute basal membrane. Treatment using a homogenizer may be performed at (a revolution speed of) 3000 rpm through 50000 rpm, preferably 10000 rpm through 40000 rpm, more preferably at about 30000 rpm.

(Thickness)

Use of an amnion for the sheet-shaped composition according to the invention enables to attain an extremely thin sheet. The sheet-shaped composition according to the invention can be prepared to be as thin as, for example, 10 μm through 500 μm. Such an extreme thinness of the sheet allows for universal use of the composition. An amnion with a part (for example, approximately 10 μm through 30 μm) of the stratum compactum of on the chorionic membrane side removed may be used to construct the sheet-shaped composition according to the invention. Alternatively, any bioabsorbable material may be coated to attain the thickness of, for example, 100 μm through 500 μm.

(Use of Adhesive Component)

In one embodiment of the present invention, on the surface of amnion, fibrinogen and thrombin (hereinafter, which are also collectively referred to as "adhesive components") is attached. Thus, when the sheet-shaped composition of the present invention is transplanted, firstly, fibrinogen is specifically hydrolyzed by thrombin so as to form fibrin, and then, fibrins are polymerized so as to form a stable fibrin clot which exhibits an adhesive effect. By virtue of the high adhesiveness, the sheet-shaped composition, once attached on a lesion, can attain a sufficient adhesion without suture, thus facilitating the surgical procedure. In the present specification, an amnion that has an epithelium and with any adhesive components attached thereto may be referred to as "amnion with attached adhesive components and epithelium" and that without an epithelium but having adhesive components attached thereto as "amnion with attached adhesive components but without epithelium".

Fibrinogen and thrombin are attached on either or both sides of the amnion depending on the application of the sheet-shaped composition of the present invention. In the case of one-sided attachment, the chorionic side-surface of the amnion (i.e. the surface opposite to its epithelium) receives the attachment, regardless of a presence or absence of the epithelium of the amnion. Accordingly, when in use, such a sheet-shaped composition thus constructed is transplanted to the application site with the side that had its epithelium facing upward. Similarly, a sheet-shaped composition for use as anti-adhesive receives its adhesive components on an either side of the amnion. On the other hand, a sheet-shaped composition that is transplanted in vivo as bioadhesive appropriately receives adhesive components on both sides of the amnion.

As mentioned below, the sheet-shaped composition of this embodiment is prepared in an appropriate state (for example, dry state or wet state) through a step of attaching fibrinogen and thrombin to the surface of amnion by considering the intended uses. Therefore, fibrin is expected to be generated from a part of fibrinogen before the sheet-shaped composition is used depending upon the state during process and/or the final state. Therefore, the sheet-shaped composition of the present invention may include fibrin or a fibrin clot generated by such a reason.

The origin of the fibrinogen and thrombin is not particularly limited. The fibrinogen and thrombin can be prepared by using blood of, for example, human, monkey, chimpanzee, bovine, horse, sheep, pig, and the like, as a starting material. Furthermore, as the fibrinogen and thrombin, a recombinant obtained by using cultured cells (for example, CHO cells or COS cells) may be used. It is preferable to use fibrinogen and thrombin derived from human (in particular, human-derived recombinant). This is advantageous from the viewpoint of safety including immunogenicity. Furthermore, by considering the stable quality and problem of infection, it is particularly preferable to use a recombinant.

It is particularly preferable to use fibrinogen and thrombin derived from blood of a patient (recipient) who is going to be subjected to transplantation of the sheet-shaped composition of the present invention. This is advantageous because immunological rejection may not be induced.

Note here that the origins of the fibrinogen and thrombin may not necessarily be the same. For example, the combination of fibrinogen derived from human blood and thrombin derived from bovine blood may be used.

The attached amount of fibrinogen and thrombin is not particularly limited. For example, the attached amount of fibrinogen can be set in the range from 0.1 mg to 50 mg per 1 $cm^2$ of amnion. Similarly, the attached amount of thrombin can be set in the range from 0.5 μm to 10 mg per 1 $cm^2$ of amnion.

Adhesive force is primarily considered when setting the attached amount of fibrinogen and thrombin. That is to say, in order to obtain the necessary adhesion force, the attached amounts of these components need to be set. On the other hand, when the attached amount of fibrinogen and thrombin is too large, immune reaction or angiogenesis may tend to be induced, although depending upon the origin of fibrinogen to be used.

Herein, in a case that a sheet-shaped composition applied to reconstruction of the ocular surface (for example, when angiogenesis due to these components after transplantation may occur) in order to suppress the induction of the angiogenesis as much as possible, it is preferable that the attached amount of these components is reduced. By setting the attached amount of these components as small as possible, the angiogenesis after transplantation can be suppressed and high therapeutic effect can be expected. As described in the below mentioned example, as a result of the investigation by the present inventors, when the attached amount of fibrinogen is about 0.5 mg or more per 1 $cm^2$ of amnion, the excellent adhesive force with respect to the ocular surface was observed. As to thrombin, even when the attached amount of thrombin is 1 μg per 1 $cm^2$ of amnion, the excellent adhesive force with respect to the ocular surface was observed. Based on these findings, the preferable range of the attached amount of fibrinogen is 0.5 mg to 20 mg per 1 $cm^2$ of amnion. Further preferable range is 0.5 mg to 10 mg per 1 $cm^2$ of amnion.

More preferable range is 0.5 mg to 6 mg (specifically, for example, about 0.5 mg, about 1 mg, and about 2 mg) per 1 cm$^2$ of amnion. Similarly, the preferable range of the attached amount of thrombin is 1 μg to 1 mg per 1 cm$^2$ of amnion. Further preferable range is 5 μg to 200 μg per 1 cm$^2$ of amnion. More preferable range is 10 μg to 100 μg (specifically, for example, about 10 μg, about 20 μg, and about 30 μg) per 1 cm$^2$ of amnion.

In one embodiment of the present invention, in addition to fibrinogen and thrombin, aprotinin is attached to the surface of amnion. Aprotinin inhibits the fibrin clot formed by the effect of thrombin from being dissolved by plasmin. Therefore, by using aprotinin together, the decomposition of the fibrin clot can be suppressed. As a result, the adhesive force can be maintained or reinforced.

The origin of aprotinin is not particularly limited. The aprotinin derived from the pancreas of, for example, bovine, horse, sheep, pig, monkey, chimpanzee, and the like. Furthermore, a recombinant aprotinin obtained by using cultured cells (for example, CHO cells or COS cells) may be used. It is preferable to use a recombinant from the viewpoint of the stable quality and problem of infection.

When aprotinin is used, the attached amount thereof is not particularly limited. For example, the attached amount of aprotinin can be set in the range from 0.1 KIU to 200 KIU per 1 cm$^2$ of amnion. We examined how a change in the attached amount of aprotinin affects the adhesion force in addition to the investigation of the above-mentioned attached amount of fibrinogen. As a result, even when the amount of aprotinin is set in the range from 1 KIU to 2 KIU, a sufficient adhesive force to the ocular surface was observed. Based on this finding, the preferable range of the attached amount of aprotinin is 1 KIU to 100 KIU per 1 cm$^2$ of amnion. Further preferable range is 1 KIU to 20 KIU per 1 cm$^2$ of amnion. More preferable-range is 1 KIU to 10 KIU (specifically, for example, about 1 KIU, about 2 KIU, and about 3 KIU) per 1 cm$^2$ of amnion. When the amount of the aprotinin is too large, the manufacturing cost is increased and furthermore, the side effect caused by the immunogenicity, etc. of the aprotinin itself may be increased. On the other hand, when the amount of aprotinin is too small, the effect of aprotinin of suppressing the deposition of fibrin clot may not be exhibited sufficiently.

In various purposes, the fibrin clot is used as an adhesive, generally with aprotinin. As a result of the investigation by the present inventors, in the sheet-shaped composition of the present invention, even if aprotinin is not used, it has been found that sufficient adhesive force with respect to a living body can be obtained. When aprotinin may not be used, a configuration can be simplified, so that advantages in terms of manufacture and cost can be achieved. In addition, it becomes unnecessary to consider the side effect caused by the immunogenicity etc. of the aprotinin itself.

(Reinforcement by Bioabsorbable Material)

Chorionic side of the amnion can be covered with any bioabsorbable material to reinforce the sheet-shaped composition of the invention. Bioabsorbable materials for such a purpose are preferably any material that is degraded and absorbed earlier relative to the amnion. For example, polygractin 910, gelatin, collagen and polylactic acid may be preferably used as bioabsorbable material described herein. The shape of the bioabsorbable material for reinforcement is not limited. Biomaterials formed into, for example, a mesh or sheet may be used to cover the chorionic side of the amnion to reinforce the amnion. The amnion during the reinforcement process may be either of a moistened state or desiccated state, although the amnion in the final product is preferably in a desiccated state in which the amnion is superior in respect of handling readiness and storage. The amnion with such reinforcement is referred to in the present specification as "hybrid amnion".

(Cell Layer)

In another embodiment of the present invention, the sheet-shaped composition comprises a cell layer on the amnion. If any adhesive components are utilized in such a form of composition, those adhesive components (such as fibrinogen) are attached to the side of the amnion where no cell layer is formed.

In this embodiment, amnion from which the epithelium has been removed is generally used. Then, at the side where the epithelium has been present, a cell layer is formed. This cell layer is formed from cells of biological origin. The origin of the cells constituting the cell layer is not particularly limited. Examples of the cells include cells derived from corneal epithelium, conjunctival epithelium, skin epidermis, hair follicle epithelium, oral mucosal epithelium, iris pigment epithelium, retina pigment epithelium, respiratory tract mucosa epithelium or intestinal tract mucosa epithelium, and the like. A cell layer may be formed by using two types or more of cells that are different from each other. Formation from two types or more of cells that are derived from different origins is also referred to as "hybridization" in this specification. The form in which cells are contained in the hybridized cell layer (state of hybridization) is not particularly limited and, for example, cells may be dispersed or some cells (or plural types of cells) may be present as a group. Furthermore, the content of cells may not be uniform over the entire cell layer. The cell layer may be a single layer or multilayer (stratified layers).

The type of cells forming the cell layer, if any, on the amnion will now be described hereinafter, taking an example of a sheet-shaped composition for reconstruction of corneal epithelium.

The hybridized cell layer contains two types or more of cells. One type of cells is referred to as first cells and the other type of cells that are different from the first cells are referred to as second cells for convenience of explanation. Firstly, autologous cells are used as the first cells. In this specification, "autologous" indicates a subject to whom the sheet-shaped composition of the present invention is to be applied, that is, a subject who undergoes transplantation (recipient). On the other hand, other than such "autologous" is referred to as "allogeneic." The type of the first cells is not particularly limited as long as the first cells can form a corneal epithelium-like mucosal epithelium layer when they are hybridized with the below-mentioned second cells. Examples of the first cells include cells derived from mucosal epithelium such as oral mucosal epithelium, conjunctival epithelium, and nasal mucosal epithelium, or cells derived from undifferentiated cells capable of constructing such mucosal epithelium (that is, mucosal epithelium stem cells). Herein, the term "derived from or of origin" is used for the purpose of specifying a starting material. Therefore, for example, cells derived from (of origin of) the oral mucosal epithelium indicates cells obtained by using oral mucosal epithelial cells as a starting material. Furthermore, in the present invention, the term "undifferentiated cells capable of constructing such mucosal epithelium" indicates cells having the potency of differentiating into cells constituting mucosal epithelium. For example, undifferentiated cells capable of constructing oral mucosal epithelium indicates cells capable of differentiating into oral mucosal epithelial cells. Specific examples of the undifferentiated cell include a precursor cell or a stem cell of cells constituting specific tissue, for example, oral mucosal epithelium or conjunctival epithelium, and the like, or an epithelial stem cell with lower differentiation.

The hybridized cell layer may include two or more different types of the first cells. For example, a cell layer may be constructed from cells derived from oral mucosal epithelium and cells derived from conjunctival epithelium.

The "oral mucosal epithelium" in the present invention may include oral crevicular mucosal epithelial part, labial part, palate part, buccal part, and the like. Whether or not the cells are derived from oral mucosal epithelium can be confirmed by using, as an indicator, the expression of keratin 4 or keratin 13 specific to oral mucosal epithelium. Alternatively, the expression of keratin 3 can be used as an indicator. This keratin 3 is known to be one of the cornea-specific keratins. However, keratin 3 was reported to be expressed also in the oral mucosal epithelial cell. Note here that it is preferable that oral mucosal epithelial cells are used as a material for producing a composition for transplantation of corneal epithelium from a viewpoint that it expresses this cornea-specific keratin, keratin 3.

On the other hand, by examining the expression of genes specific to an oral mucosal epithelial cell, it can be confirmed that cells are derived from oral mucosal epithelium.

Similarly, in the case of cells derived from a tissue other than oral mucosal epithelium, by examining the expression of the marker or gene specific to the tissue, the origin thereof can be confirmed.

Specific examples of the second cells include cells derived from corneal epithelium, conjunctival epithelium or amnion epithelium. Among them, it is preferable that the second cells are cells derived from corneal epithelium or conjunctival epithelium. This is advantageous because the cell layer constructed by cells derived from ocular surface tissue can have a property closer to that of corneal epithelium. It is particularly preferable that the second cells are derived from corneal epithelium. This is advantageous because a layer that is more similar to corneal epithelium can be obtained.

The second cells may be autologous cells or allogeneic cells. When autologous cells are used, a cell layer with no or little problem of immunological rejection can be obtained. When allogeneic cells are used, since it is easy to prepare cells, it is advantageous from the viewpoint of manufacturing. The cell layer of the present invention may include two or more different types of second cells. For example, the cell layer may be constructed in a state which includes, for example, cells derived from corneal epithelium and cells derived from conjunctival epithelium.

Whether or not the cell layer in the sheet-shaped composition of the present invention includes cells that are derived from the corneal epithelium can be confirmed by using, as an indicator, the expression of keratin 3 or keratin 12 specific to corneal epithelium. Alternatively, the expression of keratin 4 can be used as an indicator.

Similarly, in the case of cells derived from the tissue other than corneal epithelium, by examining the expression of the marker or gene specific to the tissue, the origin thereof can be confirmed.

Since the sheet-shaped composition of the present invention employs amnion as a support, it can be constructed very thinly. When the sheet-shaped composition of the present invention does not include a cell layer, the sheet-shaped composition can be prepared to the thickness, for example, in the range from 10 μm to 100 μm. When the sheet-shaped composition includes a cell layer, it can be prepared to the thickness, for example, in the range from 20 μm to 200 μm. Thus, very thin state is also one of the main features of the present invention. With this feature, the composition becomes applicable to a wide spectrum of uses. In particular, making the most of the high transparency, it can be applied to reconstruction of the ocular surface.

(State of the Sheet-Shaped Composition)

The state of the sheet-shaped composition according to the invention is not limited, and may be presented either in a moistened state (by, for example, immersing in any solution), in a frozen state, or in a desiccated state (including semi-desiccated state). Frozen or desiccated state is advantageous in respect of handling readiness and storage. When desiccated, the composition can be stored at a normal temperature (for example about 10° C. through about 35° C.). Specifically, the storage in a freezer or refrigerator until use is no longer required, and the composition will be more readily handled (storage, transportation, etc.). Of course, the composition in a desiccated state may be stored in a freezer or refrigerator, if need be.

Above all, lyophilized state provides a handling readiness and favorable attachment to the lesion where it is applied (where it filtrates and exerts its adhesiveness), thereby makes a suture after the application unnecessary (Of, course, suture may be performed to ensure attachment to the lesion). Abrogation of suture greatly reduces the burdens on patients and physicians.

Preferably, the sheet-shaped composition according to the invention is constructed utilizing an amnion, with an epithelial layer in a frozen state, with an epithelial layer in a desiccated state (lyophilized state), without an epithelial layer in a moistened state, or without an epithelial layer in a desiccated state (lyophilized state). In the present specification, an amnion with an epithelial layer in a frozen state is also referred to as "freezing-stored amnion with an epithelium", that with an epithelial layer in a lyophilized state as "lyophilized amnion with an epithelium", and that without an epithelial layer in a lyophilized state as "lyophilized amnion without an epithelium".

The sheet-shaped composition in a desiccated state is ready to handle, and, specifically, can be stored even at a normal temperature (for example about 10° C. through about 35° C.). Thus, storage in a freezer or refrigerator until use is no longer necessary, thus making its handling (such as storage or transportation) ready. Moreover, desiccation makes it possible to effectively sterilize the amnion without affecting its use. Further, since degradation of the amnion in a desiccated state is extremely low, its high quality can be maintained for a longer period of time.

It is believed that retention of the structure of basal membrane is crucial for the sheet-shaped composition of the invention to perform the function expected for it (such as a function as a substrate to form a cell layer and as a tissue-reconstruction material). In a preferable embodiment of the present invention, an amnion with its basal membrane components (Collagen IV ($\alpha 1$, $\alpha 2$, and $\alpha 5$), Collagen VII, laminin 5) retained is utilized. Presence or absence of the basal membrane components can be assayed by performing an immunostaining targeting the components at issue for detection. In one embodiment of the invention, at least one, preferably a plurality of these components, or even all of these components are detected. It is also preferable for these components to be detected at intensity not significantly different from those detected for an untreated amnion (i.e. amnion which has undergone treatment, such as freezing, post isolation from an organism).

In addition, an amnion with components of stratum compactum (Collagen I, III, V and Fibronectin) retained may preferably utilized. The retained state of the stratum compactum components may be detected an immuno-staining, similarly to the detection of the basal membrane components described above.

By adding trehalose to the amnion, the structures of the basal membrane and stratum compactum are highly maintained, even after lyophilization process.

(Presented Form)

The sheet-shaped composition according to the invention may be presented in any container, such as glass of plastic-made container, or in a packaged form in a clear film or sun-blocking sheet.

Preferably, the sheet-shaped composition of the invention is presented in a packaged form so that it has substantially no contact with oxygen. Under such a condition, the quality of the composition will cause no deterioration due to oxygen, but will be maintain at a high level for a longer period of time. A condition that "has substantially no contact with oxygen" will be attained through use of a container evacuated or filled with nitrogen gas (i.e. exhausted with nitrogen), or in the form of air-tight package using a film or sheet. In any case, the sheet-shaped composition of the invention is typically sterilized prior to use.

(Application)

The sheet-shaped composition according to the invention can be applied as, for example, transplant material for tissue reconstruction, and anti-adhesive material. Medical fields where the sheet-shaped composition of the invention can be applied include ophthalmology, digestive surgery, gynecology and dermatology.

Exemplary applications (application sites and methods, for example) of the sheet-shaped composition according to the invention will now be described with respect of situations (A) where the sheet-shaped composition of the invention comprises no cell layer and those (B) where it comprises a cell layer.

A. Situations where the Sheet-Shaped Composition Comprises No Cell Layer.

The sheet-shaped composition with no cell layer can be applied for use in, for example, reconstruction of sclera and cornea (treatment of pterygium and corneal epithelial defects), and coverage of skin (epidermis) ulcer and burn. It is also applicable as tissue reconstruction material. The term "tissue reconstruction material" herein refers to any material that can be used for reconstruction (regeneration) of any tissue of an organism. The sheet-shaped composition with no cell layer can be favorably used in a therapy for reconstructing surface tissue of organ or apparatus damaged during surgical invasion. The sheet-shaped composition of the invention is preferable particularly for reconstructing surface tissue that would cause adhesion during a normal healing process. The term "tissue reconstruction" herein typically refers to recovery of damaged lesion of surface tissue into a normal state. Alternatively, the term may comprise recovery of an organ or apparatus into a normal state by preventing re-adhesion of surface tissue of it (for example, preventing a salpinx from re-adhesion post adhesiotomy to return it to a normal state).

Exemplary tissues for reconstruction according to the invention include surface tissues of abdominal, thoracic or intrapelvic organ or apparatus (such as stomach, colon, small intestine, blind intestine, duodenum, heart, lung, oviduct, intestinum rectum, liver, ovarium, uterine), or surface tissues of intraperitoneal, intrathoracic, intrapelvic, oral, nasal, ear, or throat cavity, or ocular tissues. Accordingly, the sheet-shaped composition of the invention can be utilized in the field of digestive surgery, obstetrics and gynecology, thoracic surgery, oral surgery, ear, nose and throat surgery, and ophthalmic surgery. The sheet-shaped composition of the invention is particularly suitable as a material for reconstructing surface tissues of abdominal, thoracic or intrapelvic organ or apparatus, or abdominal cavity, thoracic cavity or surface tissues. On the other hand, the present invention is also applicable to the other fields which accompany surgical operation. Details of the sites, method, etc., of applying the sheet-shaped composition of the invention will now be described.

Use of the sheet-shaped composition of the invention applied as a tissue reconstruction material can be generally classified according to the application method and application purpose into the following three class.

(1) The Coverage (Application Method) as a Tissue Reconstruction Material/Tissue Reconstruction (Application Purpose)

Use (usage) of the composition for the purpose of reconstructing the damaged tissue surface by applying the tissue reconstruction material onto the surfaces of an organ, peritoneal, etc. Specific examples of this use are provided below in 1-1,1-4, 1-5 and 1-6.

(2) The Coverage (Application Method) as a Tissue Reconstruction Material/Anti-Adhesion (Application Purpose)

Use (usage) of the composition for the purpose of suppressing the formation of adhesion with surrounding tissues by applying an amnion onto the surfaces of an organ, peritoneal, etc. Specific examples of this use are provided below in 2-1, 3-1, 3-2, and 3-3.

(3) The Indwelling (Application Method) of a Tissue Reconstruction Material/Anti-Adhesion (Application Purpose)

Use (usage) of the composition for the purpose of suppressing the formation of adhesion by indwelling an amnion at the site where an adhesion is formed at a greater frequency. Specific examples of this use are provided below in 1-2, 1-3, and 2-2. Many of conventional anti-adhesives take this form. For example, Seprafilm currently used as an anti-adhesive takes the similar form to 1-2 below. However, Seprafilm cannot be used in the applications 1-3 and 2-2 below.

Exemplary applications of the sheet-shaped composition as tissue reconstruction material will now be specifically described (See FIG. 1).

1. Application in the Field of Digestive Surgery 1.1 Application in Reconstruction of Damaged Organ and Anti-Adhesion Various surgical operations in general leave a minute damage in organs during the procedure. Unless appropriately restored at any early stage after the surgery, destroyed chorionic structure of the damaged lesion tends to form an adhesion between organs, and may occasionally result in a loss of basic functions. Such a problem can be solved by making the most of amniotic abilities to reconstruct tissues and to prevent adhesion. Specifically, the tissue reconstruction material is used to cover damaged surface of an organ to facilitate tissue reconstruction and prevent adhesion. For such a purpose, the tissue reconstruction material constructed with, for example, cryopreserved amnion with an epithelium, cryopreserved amnion without an epithelium, lyophilized amnion with an epithelium, amnion with adhesive components attached but without an epithelium, and so on can be favorably utilized. Although it is preferable to use tissue reconstruction materials constructed with a desiccated amnion (for example lyophilized amnion with an epithelium, lyophilized amnion without an epithelium) because of its handling readiness, those which are constructed with lyophilized amnion (for example, lyophilized amnion with an epithelium, lyophilized amnion without an epithelium) can be selected for use in the area, such as heart, where the carrier requires a resiliency. As for the application method, the tissue reconstruction material is placed in position upon completion of a surgery such that it directly covers the damaged area of organ with its amniotic basal membrane facing the peritoneal cavity, and, if necessary, is immobilized, for which a suture thread such as vicryl can be used. When a tissue reconstruction material constructed by a desiccated amnion is used, the immobilization process such as suture can be done without since a high avidity is expected. Similarly, a tissue reconstruction material constructed together with adhesive components is also expected to have a high avidity. Thus, it is preferable that an immobilization of the tissue reconstruction material onto any applied site can be attained without any specific suture or other immobilization process since such a suture or other immobilization makes the procedure laborious, and may induce inflammation thereby promoting the formation of adhesion. In particular, use of tissue reconstruction material constructed with lyophilized amnion with an epithelium is most preferable since it exerts a high avidity toward applied site without any possibilities of eliciting a foreign body reaction against the adhesive components.

The procedure described above is expected to provide reconstruction of chorionic structure at an early stage after surgery, and to attain reconstruction of damaged organ while preventing adhesion.

1-2. Damaged Organ—Application for Preventing Adhesion Between Wounds.

Various surgical operations occasionally leave adhesion between intraperitoneal organ and wound. Adhesion of the intraperitoneal organ to wound physically fixes the organ, abrogates its mobility and causes clogging of the internal cavity, resulting in paralytic enterostasis. The capacity of amnion to prevent adhesion can be used to solve the problem. For such a purpose, tissue reconstruction materials constructed with cryopreserved amnion with an epithelium, cryopreserved amnion without an epithelium, lyophilized amnion with an epithelium, reinforced hybrid amnion, etc can be utilized. Since strength sufficient to prevent wrinkles is required, tissue reconstruction materials constructed with desiccated amnion is preferably used, with tissue reconstruction materials constructed with desiccated and reinforced hybrid amnion being more preferred. The application methods are as follows. Upon completion of a surgical operation, a tissue reconstruction material is inserted immediately beneath a wound, and left indwell. The tissue reconstruction material is placed in position such that the basal membrane side of its amnion faces peritoneal side, and chorionic membrane faces abdominal wall. After the application, it may be fixed by, for example, suture, though it is preferred to have it simply left indwell without any fixation.

The above procedure can successfully attain prevention of adhesion between an organ and a wound after a surgery.

1-3. Application to Prevention of Adhesion to Pelvic Floor

Colon, uterine and other extraperitoneal organs a facial part of which are not covered by peritoneal reside in intrapelvic space. Surgery on such an extraperitoneal organ may occasionally produce in the pelvic space where no peritoneal exists, allowing small intestine to collapse on pelvic floor to form an adhesion with pelvic wall. Since the adhesion, once formed, is typically difficult to detach, any preventative procedure is essential. The ability of amnion to reconstruct chorionic membrane can be used to prevent adhesion of pelvic floor. For such a purpose, tissue reconstruction materials constructed with, for example, cryopreserved amnion with an epithelium, cryopreserved amnion without an epithelium, lyophilized amnion with an epithelium, and reinforced hybrid amnion can be favorably used. The properties required for the tissue reconstruction materials are similar to those referred to in 1-2. The application method is as follows. Tissue reconstruction material is inserted into pelvic floor upon completion of a surgical operation, and lightly pressed onto peritoneal to ensure coverage. The tissue reconstruction material is placed such that the basal membrane side of the amnion faces abdominal cavity and the chorionic membrane side faces peritoneal. After the placement, the tissue reconstruction material can be immobilized by means of, for example, suture, it is preferably left unimmobilized, only serving to cover.

The above procedure can successfully attain prevention of adhesion to pelvic floor after a surgery.

1-4. Application to Reconstruction of Peritoneal Wall

Peritoneal wall may be damaged to have a defect by a plurality of surgeries or peritoneal diseases such as abdominal incisional hernia. Amnion can be used as a carrier for complementing damaged peritoneal. For such a purpose, tissue reconstruction materials constructed with, for example, cryopreserved amnion with an epithelium, cryopreserved amnion without an epithelium, lyophilized amnion with an epithelium, and amnion with adhesive components attached but without an epithelium can be favorably used. If the defect of the peritoneal is extensive and severe, it is preferable in respect of strength to use a tissue reconstruction material constructed with cryopreserved amnion with an epithelium. It is subject to application upon completion of the surgery. The tissue reconstruction material is first put on the defect area of the peritoneal so as to cover that area, with the basal membrane side of the amnion facing peritoneal cavity, and then, alternatively, the tissue reconstruction material may be immobilized by means of, for example, suture. If a tissue reconstruction material constructed with amnion with adhesive components attached thereto is used, those adhesive components may attain immobilization. The above procedure is expected to attain reconstruction of abdominal wall.

1-5. Application to Suppression of Peritoneal Metastasis

Peritoneal metastasis is a case where metastasis is caused by progression of stomach cancer, colon cancer and ovarian cancer resulting in cancer cells' spread from a particular tissue through pleural fluid or ascites fluid into coelom. Since cancers that accompany peritoneal metastasis have extremely poor prognosis, methods for suppressing metastasis have been in demand. However, any effective measures that meet such a demand are still unknown. The properties of amnion are expected to be exploitable to suppress metastasis. Dorsal mesogastrium, diaphragm, and mesentery, amongst others, are known as sites where cancer cells cause metastasis at a greater frequency. These milky spots, so to speak, can be pre-covered with tissue reconstruction material to form a barrier to successively attain suppression of metastasis. For such a purpose, tissue reconstruction materials constructed with, for example, cryopreserved amnion with an epithelium, cryopreserved amnion without an epithelium, lyophilized amnion with an epithelium, and amnion with adhesive components attached but without an epithelium can be favorably used. However, use of tissue reconstruction materials constructed with lyophilized amnion with an epithelium is preferred because of their readiness in handling. As an exemplary application method, the tissue reconstruction material can be placed such that it wraps around the tissue of interest and covers the application site. Alternatively, the tissue reconstruction material can be immobilized on the application site by means of suture with a patch intervening a portion of it, or by means of adhesive components attached onto the amnion. The timing for application of the tissue reconstruction material may be after metastasis as a result of progression of cancer, or before any spread (Preliminary use).

1-6. Application to Prevention of Recurrent Adhesion

Ileus may be caused after laparotomy, by adhesion between bowels or between a bowel and abdominal wall, leading to a bending thereabout which causes passage disorder and resulting dysfunction. Even if the adhesion is successfully disrupted, the once adhered tissues, especially those tissues which caused a severe inflammation and cicatrized have defective chorionic membrane, and, therefore, typically cause re-adhesion post surgery. Amnion can be used to prevent re-adhesion post surgery, and facilitate repair and reinforcement of the defective chorionic membrane. For such a purpose, tissue reconstruction materials constructed with, for example, cryopreserved amnion with an epithelium, cryopreserved amnion without an epithelium, lyophilized amnion with an epithelium, and amnion with adhesive components attached but without an epithelium can be favorably used. However, use of tissue reconstruction materials constructed with lyophilized amnion with an epithelium is preferred because of their readiness in handling. As an exemplary application method, after laparotomy and when the adhesion has been physically disrupted, the tissue reconstruction material can be placed such that it wraps around the bowel like a tube. The tissue reconstruction material is placed in position such that the basal membrane side of the amnion faces abdominal cavity. Immobilization that typically occurs after that placement may be in the form of suture between the organ and the amnion or between the amnions (making the amnion a tube) using a suture such as vicryl. Alternatively, the tissue reconstruction material may be left indwell without any suture. When tissue reconstruction materials constructed with an amnion with adhesive components attached thereto is used, those adhesive components may serve to attain the immobilization. It is preferable that immobilization of the tissue reconstruction material to the applied site is attained without a separate immobilization process such as suture, since such a suture or other immobilization makes the procedure laborious, and may induce inflammation thereby promoting the formation of adhesion. In particular, use of tissue reconstruction material constructed with desiccated amnion is most preferable since it exerts a high avidity toward applied site without any possibilities of eliciting a foreign body reaction against the adhesive components.

The procedure described above is expected to provide reconstruction of chorionic structure at an early stage after surgery while preventing re-adhesion.

2. Application in Obstetrics and Gynecology

2-1. Application to Salpingemphraxis

Adhesion of salpinx to organs such as peritoneal causes blockage of the salpinx and makes oval passage difficult, resulting in infertility. Amnions can be used to prevent adhesion of salpinx. Tissue reconstruction materials of the invention can be applied for such a purpose in the following procedure. Adhesion is firstly disrupted and a typical fimbrioplasty is performed. After the surgery, but before closing the operative wound, the area of salpinx is covered with tissue reconstruction material. For such a purpose, tissue reconstruction materials constructed with, for example, cryopreserved amnion with an epithelium, cryopreserved amnion without an epithelium, lyophilized amnion with an epithelium, and amnion with adhesive components attached but without an epithelium can be favorably used. However, use of tissue reconstruction materials constructed with lyophilized amnion with an epithelium is preferred because of their readiness in handling. As an exemplary application method, the tissue reconstruction material can be placed such that it wraps around the tissue of interest and covers the application site. Alternatively, the tissue reconstruction material can be immobilized on the application site, by means of suture with a patch intervening a portion of it, or by means of adhesive components attached onto the amnion.

2-2. Application to Prevent Adhesion of Pelvic Floor

Uterine inside pelvis is an extraperitoneal organ, and an approximately 50% of its surface is not covered with peritoneal. Therefore, hysterectomy produces sites where no peritoneal exists, causing adhesion between pelvic floor and small intestine. Amnions can be used to prevent the adhesion of pelvic floor. The form and, application methods of the tissue reconstruction materials used for such a purpose are similar to those described in 1-3.

3. Application to Ophthalmic Field

3-1. Application to Surgery to Treat Glaucoma

Glaucoma is a disease where optic nerves are affected to cause narrowing of visual field and low vision. Glaucoma is treated by severing travecula to form a new adieus humour discharge system. However, such an operation occasionally results in adhesion between sclera and conjunctiva and produces a poor outcome. Use of amnions may be effective for such a problem. In particular, after a typical operation of severing travelula, the tissue reconstruction material is inserted beneath the conjunctiva. For such a purpose, tissue reconstruction materials constructed with, for example, cryopreserved amnion with an epithelium, cryopreserved amnion without an epithelium, lyophilized amnion with an epithelium, and amnion with adhesive components attached but without an epithelium can be favorably used. However, use of tissue reconstruction materials constructed with lyophilized amnion with an epithelium is preferred because of their readiness in handling. After the application, the tissue reconstruction material may be immobilized to applied site by, for example, suture.

3-2. Application to Symblepharon

Symblepharon is a disorder where cicatrices are formed between palpebral conjunctive and eye ball, causing adhesion between eyelid and eye ball. Symblephalon typically accompanies an extensive damage on eye surface, and any disruption of adhered tissue entail recurrence of the symblephalon. Amnions can be used to suppress symblepharon. As an exemplary application method, the adhesion lying between eyelid and eye ball is disrupted, and the cicatrized conjunctival tissue is detached, thereby exposing sclera, which is then covered with tissue reconstruction material. For such a purpose, tissue reconstruction materials constructed with, for example, cryopreserved amnion with an epithelium, cryopreserved amnion without an epithelium, lyophilized amnion with an epithelium, and amnion with adhesive components attached but without an epithelium can be favorably used. However, use of tissue reconstruction materials constructed with amnion with adhesive components attached without an epithelium is preferred, for example, because of their readiness in handling. Immobilization of the used tissue reconstruction material onto applied site is attained typically by the adhesive components. The site, covered by the tissue reconstruction material, may be on either side of eyelid or sclera.

3-3. Application to Recurrent Pterygium

Pterygium is a disorder where conjunctival tissue cause an abnormal hyperplasia, and those hyperplastic tissues adhere to corneal, resulting in astigmatism and low vision. Amnions may be effective for this disorder. As an exemplary application method, pterygium tissue is disrupted to expose sclera, which is then covered with tissue reconstruction material. For such a purpose, tissue reconstruction materials constructed with, for example, cryopreserved amnion with an epithelium, cryopreserved amnion without an epithelium, lyophilized amnion with an epithelium, and amnion with adhesive components attached but without an epithelium can be favorably used. However, use of tissue reconstruction materials, which are constructed with adhesive components attached without an epithelium, is preferred because of their readiness in handling. Immobilization of the used tissue reconstruction material onto applied site is attained typically by the adhesive components.

B. Application of the Sheet-Shaped Composition Comprising Cell Layer

Those sheet-shaped compositions, which comprises cell layer, can be applied to reconstruction of corneal and retina (in treatment of, for example, Stevens-Johnson syndrome, thermo-chemical injuries, ophthal pemphigoid, ablatio retinae, degeneration maculae luteae senile, glaucoma, and degeneration pigmentosa retinae), treatment of epidermal diabetic ulcer (epidermis), bullous epidermolysis, or ambustion.

(Producing Method of Sheet-Shaped Composition)

Another embodiment of the present invention relates to a producing method of sheet-shaped composition. The producing method according to the invention comprises the following steps of; (a) preparing an amnion, and (b) adding trehalose to the amnion.

1. Preparation of Amnion: Step (a)

"Amnion" is a membrane covering the outermost layer of the uterus and the placenta in mammals, and including a basal membrane and an epithelium layer formed on parenchymal tissue rich in collagen. It is preferable that human amnion is used as amnion. Human amnion can be collected by, for example, human embryonic membrane, placenta, etc. obtained at the time of afterbirth at delivery. Specifically, the human amnion can be prepared by treating and purifying the integrated material including human embryonic membrane, placenta, and umbilical cord obtained right after delivery. The treating and purifying method can employ a well-known method, for example, a method described in Japanese Patent Unexamined Publication No. H5-5698, etc. That is to say, amnion is detached from the embryonic membrane obtained at delivery and remaining tissue is removed by a physical treatment such as ultrasonic cleansing and an enzyme treatment, and the like. Then, appropriate washing process is carried out and thus the human amnion can be prepared.

The thus prepared human amnion can be cryopreserved before use. The human amnion can be frozen in a liquid mixing equal volume ratio of DMEM (Dulbecco's modified Eagle's medium) and glycerol at, for example, −80° C. By cryopreservation, not only the improvement in operation property but also reduction of the antigenicity can be expected.

Intact amnion may be used but it is preferable that amnion from which epithelium has been removed by a scraping treatment, etc. is used. By removing the epithelium, antigenicity is reduced. For example, cryopreserved human amnion is thawed and then subjected to a treatment with EDTA or proteolytic enzyme so as to loosen the adhesion between cells. Then, epithelium is scraped by using a cell scraper, etc. Thus, the human amnion from which epithelium has been removed can be prepared.

Preferably, an epithelium of amnion is removed by a method comprising the following step of;
(1) preparing an amnion isolated from an organism;
(2) subjecting the amnion to freeze and thawing process;
(3) subjecting the amnion post the freeze and thawing process to tryptic treatment; and
(4) washing the amnion post the tryptic treatment.

Similarly to the conventional, manual removal of epithelium, the removal of epithelium according to the present invention allows a complete removal of epithelium with minimal damage on basal membrane. In particular, the removal of epithelium allows a complete removal of epithelium, while providing an amnion having a basal membrane with its native-structure favorably maintained. Such an amnion can serve favorably, for example as medium (base) for culturing cells. On the other hand, the following method of removing an epithelium is extremely ready to handle and less time-consuming, relative to conventional, manual removal. Moreover, it facilitates to treat a multiple of amnion at a time. Further, since it requires no special skills, automation thereof is ready.

Each step of the instant method for removing epithelium will be described below in detail.

(Preparation of Amnion: Step 1)

In step (1), an amnion is prepared, which is herein preferably human amnion. Human amnion can be harvested from, for example, human fetal membrane or placenta obtained during afterbirth of a delivery. Specifically, a solid mass comprising human fetal membrane, placenta and umbilical cord obtained immediately after a delivery is treated and purified to prepare human amnion. Such a method for preparing human amnion may be performed by any known method, such as that described in Japanese Patent Publication No. 5-56987. These steps are performed typically in the following procedure.

(1) Harvesting of Amnion

A part of placental tissue is harvested during delivery, and an amniotic tissue is manually detached from that placental tissue. Alternatively, the amniotic tissue may be temporarily frozen.

(2) Removal of Blood Cell Components and Others

Any blood cell components that are left on the amnion is washed away with physiologic saline and removed. In addition, chorionic membrane is manually detached and removed. Thus, although it is preferable to make the amnion free from blood cell components and chorionic membrane at this stage, the removal of blood cell components and/or detachment of chorionic membrane may occur after a freeze-thawing process (step 2).

The human amnion thus prepared can be frozen and stored until next process. The freezing of human amnion can be performed at −80° C. in a mixture of DMEM (Dulbecco's modified Eagle's medium) and glycerol in an equivalent amount in volumetric ratio. Cryopreservation is expected to not only improve handling readiness, but also reduce antigenicity.

(Securing into Frame)

The amnion prepared in the above procedure is preferably secured into a frame, and subjected to following process since by securing into a frame, the amnion is made ready to handle.

Exemplary methods of securing the amnion are shown in FIG. 2. In FIG. 2a, two pieces of frame (1, 2) are used. An amnion 10 is spread wide and secured into the two frames with its edge clamped between the frames. In FIG. 2b, a frame 3 and a plate-like member 4 are used to secure an amnion 10. The amnion 10 is placed and spread wide on the plate-like member 4, with upper side of the amnion 10 facing upward. Then, the frame 3 is mount over the amnion 10, clamping the edge of the amnion 10 between the plate-like member 4 and the frame 3. As a result, only the epithelium side of the amnion 10 is exposed. Accordingly, only the epithelium side of the amnion 10 can be brought into contact with tryptic solution in the following tryptic treatment (for example by adding tryptic solution inside the frame 3). This enables the tryptic treatment to be performed without affecting other portions (stratum compactum and basal membrane of the amnion) than the epithelium. In other words, the epithelium of the amnion can be subjected to the tryptic action, while protecting stratum compactum and other portion of the amnion against the tryptic action.

(Freeze-Thawing Process: Step 2)

In this step, the amnion is temporarily frozen, and then thawed. This freeze-thawing process facilitates removal of the amniotic epithelium in the following tryptic treatment. This is thought to be due to loosening of the adhesion (binding state) between the amniotic epithelium and the basal membrane.

Freezing temperature may be in the range of about −20° C. through about −80° C. In consideration of sufficient freezing condition and availability of universal freezer, freezing at about −80° C. is preferable. On the other hand, thawing may be at a temperature in the range of about 4° C. through about 50° C. The thawing temperature is preferably about 37° C.

It is preferable to repeat the freeze-thawing process. Repetition of this process adds to the effect of freeze-thawing process by facilitating the removal of epithelium in the following tryptic treatment. However, it is expected that the repetition beyond what is necessary will adversely affect any portions other than epithelium. Accordingly, the freeze-thawing process is preferably repeated in the range of two through four times. The inventions have found that repetition of freeze-thawing process twice with freezing at −80° C. and thawing at 37° C. yields a necessary and sufficient condition. Based on this knowledge, it is believed that, under the condition of freezing at −80° C. and thawing at 37° C., repetition of freeze-thawing twice is preferable.

The conditions for each round of repeated freeze-thawing process (freezing temperature and thawing temperature) may be wholly the same, partly the same, or totally different. In view of handling readiness, the conditions are preferably the same.

(Tryptic Treatment: Step 3)

In this step, the amnion post the freeze-thawing process is treated with trypsin. The trypsin treatment is performed by contacting the amnion with tryptic solution. An exemplary tryptic solution is that with a tryptic concentration of about 0.01% (w/v) through about 0.05% (w/v). Preferably, a tryptic solution at a tryptic concentration of about 0.02% (w/v) is used. If the tryptic concentration of a tryptic solution is too low, the tryptic action is not sufficiently exerted. On the other hand, if the tryptic concentration is too high, the tryptic action is exerted favorably on the amniotic epithelium, but inadvantageously extends beyond the epithelium to damage the underlying amniotic stratum compactum and basal membrane.

Trypsin may be of any origin, including bovine, porcine, human and any other origins commercially available. Trypsin-EDTA (Invitrogen), and Trypsin 1:250 (Sigma), for example, can be favorably used.

Tryptic solution may typically have any chelators added thereto, which is not always necessary. Exemplary chelators are EDTA, NTA, DTPA, EDTA, GLDA or any combination thereof. Chelators may be at concentration of, for example, about 0.1 mM through about 0.6 mM.

It is preferable that the tryptic treatment is performed under such conditions that only the epithelial side of the amnion is brought into contact with tryptic solution in order to protect other portions than the amniotic epithelium against tryptic action. The epithelial side of the amnion exclusively can be brought into contact with tryptic solution by, for example, immersing the amniotic epithelial side in tryptic solution, adding or applying tryptic solution onto the amniotic epithelial side, or blocking the chorionic side of the amnion, so as not to contact with tryptic solution before immersing wholly in tryptic solution. As described above, use of the amnion pre-secured into a frame as shown in FIG. 2b (framed amnion) can attain the exclusive contact of the epithelial side of the amnion with tryptic solution, for example by immersing the framed amnion in tryptic solution since only the epithelial side is exposed. This method also has an advantage of simplifying the tryptic treatment by making it a simple operation of immersing a framed amnion. In addition, use of a framed amnion can take other various forms of tryptic treatment than immersing the framed amnion, wholly along with the frame, into tryptic solution, for example by immersing only the epithelial side of the amnion in tryptic solution (for example by facing the epithelial side of the amnion downward to be immersed in tryptic solution), by adding tryptic solution into the frame, or by applying the tryptic solution onto the epithelial side of the amnion, to bring only the epithelial side into contact with tryptic solution.

The time period for tryptic treatment (time period for contacting with tryptic solution) may be, for example, in the range of about 5 minutes through about 60 minutes. Preferably, the time period is from about 10 minutes to about 20 minutes, more preferably about 15 minutes. If the treatment time period is too short, tryptic action is not sufficiently exerted, resulting in an insufficient removal of the amniotic epithelium. On the other hand, if the time period is too long, the tryptic action may extend to and damage basal membrane and stratum compactum of the amnion.

The temperature at which the tryptic treatment is performed by from about 25° C. to about 42° C. such that trypsin acts favorably.

During the contact of tryptic solution, it is preferred to maintain the amnion at a stand-still condition under which tryptic solution may hardly permeate through basal membrane and stratum compactum. Alternatively, the tryptic treatment may be performed in a plurality of steps.

(Washing: Step 4)

After the amnion is contacted with tryptic solution in the manner described above, it is subjected to washing wherein the tryptic solution attached is removed and, at the same time, so is the amniotic epithelium (epithelial cells). This washing of the amnion after tryptic treatment may be done by leaving it under an appropriate stream of solution (for example running water), by shaking (for example shaking up and down) it while immersing it in an appropriate solution and, or by subjecting it to ultrasound or other vibration while immersing it in an appropriate solution. The washing solution may be, for example, saline solution, phosphate buffered saline, pure water and DMEM.

The amnion after washing may be stored in a refrigerator or freezer until use. For example, the amnion can be stored with it immersed in a solution containing glycerol (for example, DMEM (Dulbecco's Modified Eagle Medium: GIBCOBRL) containing 50% glycerol).

2. Addition of Trehalose: Step (b)

Addition of trehalose to the amnion can be performed by immersing the amnion in trehalose solution. For example, the amnion is immersed in a solution of 5% (w/v)-20% (w/v) trehalose in distilled water or phosphate buffered saline (PBS (−)). The temperature during the immersion is, for example, from about 4° C. to about 37° C. The immersion time period is, for example, from about one hour to one day. The trehalose used may be, for example, "Toreha" (Registered Trademark) available from Hayashibara Corp. or "Torehainochi" available from H plus V Lifescience Corp.

Addition of trehalose to the amnion can take other forms such as, for example applying trehalose solution to the amniotic surface, spraying trehalose solution to the amniotic surface and adding trehalose directly onto the amniotic surface.

The step of removing an epithelium from the amnion (for example the steps 2 through 4 above) may have a preceding step of adding trehalose.

3. Freezing Process or Desiccation Process: Step (c)

In one embodiment of the invention, the amnion, once added with trehalose, is frozen or desiccated. This process improves the preservability and handling readiness. Moreover, the desiccation process greatly enhances the preservability and handling readiness of resulting sheet-shaped composition. Further, a change of the surface profile of the amnion that accompanies the desiccation is expected to crease the affinity (adhesiveness) of the amnion to tissues of a living organism. The desiccation process of the amnion is preferably performed through lyophilization since this process mitigates the reduction of amniotic flexibility. In addition, lyophilization process is preferable in respect of maintaining the structure of the amniotic basal membrane components. The lyophilization process removes the moisture contained in a frozen sample (for example, a sample frozen at about −40° C.) through sublimation under a low atmospheric condition (vacuum) where a boiling point lies in the range of about −20° C. (107 Pa, 0.8 Torr) through about −50° C. (4 Pa, 0.03 Torr). Since lyophilization dehydrates uniformly from inside, and achieves a high dryness, native function and profile can be highly maintained even after the desiccation. Further, lyophilization has advantages of, for example, 1. having a less deterioration during the process, 2. being ready to making it aseptic, 4. and yielding an improved desiccated result which has a high ability to regain its original profile.

Lyophilization can be performed by a lyophilizer comprising a vacuum chamber, cooling and heating apparatus, and exhauster (cold trap and vacuum pump). A numerous lyophilizers are commercially available, any of which can be utilized for performing the instant lyophilization. The conditions for the lyophilization can be set according to any instruction attached to the lyophilizer used and in consideration of the size and a desired dryness of the sample that undergoes the desiccation. The dryness may be set such that, for example, its water activity (AW) becomes less than 0.5.

Desiccated amnion with a desired size and shape can be obtained by severing or cutting out the desiccated amnion. The desiccated amnion thus obtained may be secured to a support or frame.

In one embodiment of the present invention, the desiccated amnion obtained through the desiccation process is contained in any suitable container such that there is substantially no contact with oxygen. Containment into a package in such a state substantially sequestered from oxygen attains a non-epithelium-containing desiccated amnion having an extremely high preservability.

For example, the amnion after desiccation is contained in a suitable container and, for example, the air inside the container aspirated and removed to evacuate or replace with nitrogen, thereby putting the amnion into a packaged substantially sequestered from oxygen. Alternatively, the container may also contain deoxidant to remove the remaining oxygen. These methods may optionally be combined. An exemplary container is, for example, a bag- or tube-like container (two sheets may be superposed to each other with their periphery sealed) made of plastic synthetic resin or a bottle-like container made of glass or other inorganic material.

The freezing process or desiccating process may be preceded or followed by a step of covering the chorionic side of the amnion with bioabsorbable material to strengthen the amnion. Exemplary bioabsorbable materials are polyglactin 910, gelatin, collagen, and poly-lactic acid.

4. Sterilization Process Step: Step (d)

Sterilization process minimizes the risk of bacterial contamination. For example, EOG (Ethylene oxide gas), UV (Ultraviolet), γ-ray treatment can be used to sterilize the amnion. γ-ray sterilization is most preferable amongst these because of its low tendency to decrease amniotic physical properties. Dose for the γ-ray sterilization may be, for example, from 2 kGy to 50 kGy, preferably from 10 kGy to 30 kGy, more preferably from 15 kGy to 5 kGy. It is preferable to perform the sterilization process after the amnion which underwent the series of process has been contained in a container or wrapped in a film or sheet, etc. Accordingly, the sterilization process is preferably preceded by a step of containing the amnion in a container, etc. The amnion is preferably contained or wrapped under a condition having substantially no-contact with oxygen for minimizing deterioration of quality and allowing storage for a longer period of time.

5. Attachment of Adhesive Components: Step (e)

In one embodiment of the invention, fibrinogen and thrombin are attached to the surface of the amnion. The attachment of these components can be performed after the desiccation process described above. Use of desiccated amnion allows for a favorable attachment of fibrinogen and other adhesive components.

The attachment of fibrinogen and thrombin to the surface of the amnion is performed independently or simultaneously. Methods of attachment are not limited. An exemplary method of attachment is by applying, dropping or spraying a solution of the attached components to the amniotic surface, or by immersing the amnion in a solution of the attached components. Alternatively, fibrinogen itself (or thrombin itself) or any components deposited after dissolving fibrinogen (or thrombin) in an appropriate solvent is added (sprinkled) on the amniotic surface to attach fibrinogen (or thrombin) to the amniotic surface.

Preferably, a mixture of these two components is prepared and, for example, by applying or dropping the mixture to attach fibrinogen and thrombin to the amniotic surface. Specific exemplary methods of simultaneously attaching the two components are described below.

A solution of fibrinogen is first prepared. Specifically, fibrinogen is dissolved in ethanol (for example 94% ethanol) or other solvent (solvent medium) at a desired concentration. Besides ethanol, alcohols such as anhydrous ethanol, isopropanol, methanol and acetone can be used as solvent. Meanwhile, thrombin solution is prepared separately in the same manner. Exemplary solvents that can be used in this case are ethanol (such as 99.5% ethanol), anhydrous ethanol, isopropanol, methanol and other alcohols and acetone.

Next, the fibrinogen solution and thrombin solution prepared in the above described manner are mixed. The mixture thus obtained is used to perform applying, dropping or other procedure on the amnion as described above. If the described mixture of fibrinogen solution and thrombin solution is used for the attachment procedure, it is preferable to ensure that the water content in the mixture is at too high a level. If the water content is too high, a reaction between fibrinogen and thrombin occurs before the attachment procedure, hampering that procedure. In addition, in order to attain a favorable adhesiveness after transplant, the fibrinogen and thrombin attaching to the amnion has preferably no preceding action therebetween. In consideration of the above factors, a solvent for each of fibrinogen and thrombin is preferably water-soluble and volatile, and has less water content.

While application or dropping, for example, of fibrinogen solution and thrombin solution, or a mixture of fibrinogen and thrombin is typically performed uniformly over the entire region of the amniotic surface, it may be performed on a limited region (for example by spotting on a plurality of regions with a distance therebetween, or by placing them only over the periphery), or with their attached density varied.

In the above procedure, the attachments of fibrinogen and thrombin are performed simultaneously. However, each of these components may be attached in separate steps. Specifically, attachment of fibrinogen and attachment of thrombin may take place in two steps. However, in respect of simplifying the procedure and attaining a uniform distribution of attached fibrinogen and thrombin, it is preferable to use a mixture of fibrinogen and thrombin to perform the attachment in one single step.

Fibrinogen and thrombin can be prepared from blood according to conventional methods. Alternatively, recombinant fibrinogen and other components can be used, in which case any appropriate culture solution or lysis solution of cultured cells can be used according to conventional methods. Alternatively, any commercially available fibrinogen, or other components can be used. For example, fibrinogen derived from human can be purchased from Baxter Corp. Similarly, thrombin derived from human can be purchased from Baxter Corp.

In addition to fibrinogen and thrombin, aprotinin may be attached to the amniotic surface. Specifically, in the instant embodiment, a step of performing attaching aprotinin (step b-1) is further performed. The attachment of aprotinin can be performed in the similar means and procedure to the attachment of fibrinogen, etc. Specifically, application, dropping, spraying, immersion and other procedure using the aprotinin solution results in attachment of aprotinin to the amniotic surface. The aprotinin solution can be prepared by dissolving aprotinin in sodium chloride solution (for example 0.85% solution), potassium chloride solution, calcium chloride solution, magnesium chloride solution, etc.

Aprotinin can be prepared from bovine pancreas according to conventional methods. Alternatively, recombinant aprotinin can be used, in which case any appropriate culture solution or lysis solution of cultured cells can be used according to conventional methods. Alternatively, any commercially available aprotinin may be used. For example, aprotinin of bovine origin can be purchased from Bayer Pharmaceuticals. Although the step of attaching aprotinin can be performed singularly, the steps of attaching fibrinogen and thrombin are preferably performed simultaneously since the procedure for attaching adhesive components is facilitated as a whole. It is further because that a more uniform distribution of fibrinogen, thrombin and aprotinin attached on the amniotic surface can be attained. For example, by preparing a mixture of fibrinogen, thrombin and aprotinin and, for example, applying the mixture, simultaneous attachment of these components to the amnion can be attained. The order of mixture of these three components is not limited.

The attachment of fibrinogen, etc. is performed on either or both sides of the amnion. In the former case, the attachment of fibrinogen, etc. is performed on the surface (i.e. chorionic side) opposite to the epithelium (the side where an epithelium was present), irrespective of the presence or absence of the epithelium on the amnion.

After fibrinogen and thrombin (plus aprotinin in some occasion) have been attached, desiccation process is performed, as necessary, to yield a sheet-shaped composition with a high stability in storage and with a form favorable for handling (transportation, transplant, etc.).

The desiccation process may adopt any typical desiccation procedure, such as air-drying, vacuum-drying, suction-drying, lyophilization, and so on.

(Method for Producing Sheet-Shaped Composition Comprising Cell Layer)

In one embodiment of the invention, cell layer utilizing tissue-derived cells are formed on the amnion. The step of forming cell layer can be performed in the following procedure. Any appropriate tissue-derived cells are prepared (step of preparing tissue-derived cells). The tissue-derived cells are selected so as to accommodate the application of resulting sheet-shaped composition. For example, in order to produce a sheet for reconstructing skin epidermal tissues, skin epidermal cells (including their stem cells and precursor cells) and follicular epithelial cells are preferably used. Similarly, in order to reconstruct corneal epithelial tissues, corneal epithelial cells (including their stem cells and precursor cells) are preferably used, and, in order to reconstruct mucosal epidermal tissues, mucosal epithelial cells (including their stem cells and precursor cells) are preferably used. Exemplary mucosal epithelial cells are oral mucosal epithelial cells, intestinal mucosal epithelial cells and air duct mucosal epithelial cells.

Methods for preparing tissue-derived cells are hereinafter described, taking examples of skin epidermal cells, corneal epithelial cells, oral mucosal epithelial cells, intestinal mucosal epithelial cells, and air duct mucosal epithelial cells.

(Skin Epidermal Cell)

Firstly, when the skin is collected, a site to be collected is disinfected with disinfectant such as povidone iodine prophylactically in advance and antifungal agent is externally applied thereto, followed by collecting a small skin piece in accordance with skin biopsy. In culturing epidermal keratinocytes, fatty tissue and dermis are removed from the skin piece as much as possible by using scissors and washed with Dulbecco's phosphate buffer (PBS) several times and soaked in 70% ethanol for one minute for sterilization. The piece is cut into a strip shape, soaked in Dispase solution and stood still over night at 4° C. Then, epidermis is peeled off from the dermis. The peeled epidermis is washed, followed by disentangling the epidermal piece so as to prepare suspending solution of epidermal keratinocyte. The cells are suspended in a serum free culture medium and seeded on a collagen-coated dish, and subculture is carried out.

(Corneal Epithelial Cell)

Corneal epithelial cells can be obtained from a corneal limbus tissue. For example, endothelial cells are peeled off and removed from corneal limbus tissue, and conjunctiva is excised so as to form a single cell suspension. Then, this is preserved in a nitrogen tank, and then rapidly melted at 37° C. so as to adjust a corneal epithelial cell suspending solution. If necessary, subculture is carried out. For subculture, for example, EpiLife™ (Cascade), an MCDB153 medium (NISSUI PHARMACEUTICAL CO., LTD.), which are serum free media, and media produced by modifying the amino acid composition, etc. of the above-mentioned media can be used.

(Oral Mucosal Epithelial Cell)

As the oral mucosal epithelial cells, cells existing in the dental root part (oral crevicular mucosal epithelial cells), cells of labial part, cells of palate part, cells of buccal part, and the like, can be used. Among them, it is particularly preferable to use oral crevicular mucosal epithelial cells because of the high proliferation ability and low antigenicity. The oral mucosal epithelial cells can be collected by ablating a site where targeted cells exist with the use of a scalpel, or by scraping it out. Oral crevicular mucosal epithelial cells can be collected by separating oral mucosal epithelial cells from the enamel cement transition portion and collecting the cells from the obtained tissue piece. Note here that in order to remove impurities such as connective tissue, preferably, a treatment with enzyme such as dispase or trypsin, etc., filtration treatment are carried out.

(Intestinal Tract Mucosa Epithelial Cell)

The intestinal tract mucosa epithelial cells are collected from intestinal tract epithelium tissue to an endoscope of the large intestine, or by usual technique at the time of abdominal section. Furthermore, epithelial cells can be removed from tissue by laser capture microdissection. The technique of the present invention can be applied to sheet-shaped composition produced by using epithelial cells from all the human digestive tract such as esophagus, upper stomach, duodenum, small intestine, and large intestine. When ulcer, inflammation, or the like, causes injuries of human digestive tract epithelium, cells derived from bone marrow play a roll as a rescue with respect to emergency, so that the epithelium is repaired. The digestive tract epithelial cells, although a part of them, are also made from bone marrow. In this sense, the present invention can be regarded to have significance that is equivalent to that using corneal epithelial cells. In general, an epithelial cell made of bone marrow, which is usually only several cells per 1000 cells, are increased 50 to 100 times in the process in which ulcers (wounds) on the internal surface of the digestive tract, which are generated by, for example, gastric ulcer and colitis, are being cured. It is determined that about 1 of 10 digestive tract epithelial cells are derived from the bone marrow. The sheet-shaped composition derived from the digestive tract mucosa epithelial cells are extremely significant because they urge the regeneration of intestinal tract epithelium with respect to ulcer and inflammation of intestine diseases which are designated intractable diseases, that is, severe intestinal tract infectious diseases such as ulcerous colitis, Crohn's disease, Behchet's disease, and the like. The effectiveness with respect to intestinal tract allergy can be expected.

(Respiratory Tract Mucosa Epithelial Cell)

Respiratory tract mucosa epithelial cells can be easily obtained from biopsy tissue of the respiratory tract mucosa. Similar to the above-mentioned tissue, in order to remove impurities such as connective tissue, it is preferable that treatment with enzyme such as Dispase, trypsin, and the like, or filter treatment is carried out. The respiratory tract mucosa epithelial cells play an important role for pathologic conditions of various infectious diseases via biosyntheses and release of β defensin. Furthermore, respiratory tract mucosal epithelium also plays an important role in asthma or allergic disease. Providing sheet-shaped composition produced by the respiratory tract mucosa epithelial cells according to the present invention to the respiratory tract mucosa having tissue disorder would lead to not only carrying out emergency treatment but also providing artificial respiratory tract. In particular, immunosuppression effect of the sheet with amnion is useful.

It is preferable that after tissue is collected, oral mucosal epithelial cells, intestinal tract mucosa epithelial cells, and the like, are subjected to a treatment with enzyme such as Dispase, trypsin, and the like, or filter treatment in order to remove impurities such as connective tissue.

It is preferable that the cells of biological origin are prepared from a person (recipient) who undergoes transplantation. That is to say, it is preferable that a donor of cells of biological origin is identical to a recipient of the sheet-shaped composition. By using such autologous cells, problem as to immunological rejection is avoided.

The prepared cells of biological origin are seeded onto amnion (step of seeding cells of biological origin onto amnion), followed by culturing thereof (step of culturing and proliferating the seeded cells of biological origin).

In this embodiment, it is particularly preferable to use amnion from which the epithelium has been removed. By removing the epithelium, the reduction of antigenicity can be expected. Furthermore, since unnecessary cells are removed in advance, target cell layers can be formed excellently. When amnion from which the epithelium has been removed is used, it is preferable that cells of biological origin are seeded on the side of the exposed surface from which the epithelium has been removed (that is to say, side of the basal membrane). It is thought that this side of the surface is rich in type IV collagen, so that the proliferation and stratification of the seeded cells of biological origin can proceed excellently.

Herein, by using two types of cells, a hybridized cell layer may be formed. A method of forming a cell layer in such a case is described in detail hereinafter, taken the case where a sheet-shaped composition for reconstructing the corneal epithelium as an example.

Firstly, one of the cell types used for forming a cell layer (the first cells), cells derived from mucosal epithelium such as oral mucosal epithelium, conjunctival epithelium, and nasal mucosal epithelium, or undifferentiated cells capable of constructing such mucosal epithelium can be preferably used. On the other hand, as the cell type (the second cells) used for forming a cell layer together with the first cells, corneal epithelial cells, conjunctival epithelial cells, or amnion epithelial cells can be preferably used. These cells can be collected from a living tissue in which these cells are present. Specifically, for example, a part of the tissue in which target cells exist is collected by using a surgical knife and the like, to the treatment such as removing of the connective tissue, separation of cells, and the like, and formed in a state of the cell suspending solution (suspension). Note here that as the first cells, two or more different types of cells may be used. Similarly, as the second cells, two or more different types of cells may be used.

It is suggested that oral mucosal epithelium that is suitable for a collection source of the first cells includes stem cells. Therefore, it is thought that the oral mucosal epithelium can easily carry out differentiation induction for forming cells capable of forming an epithelium-like cell layer. Furthermore, the use of oral mucosal epithelial cells has advantages that they are collected easily, a large number cells can be collected, and furthermore, even in the case of treating corneal disease occurring in bilateral eyes, autologous cells can be used so as to prepare a transplantation material, and the like. In particular, also for patients from whom corneal epithelial cells cannot be collected, transplantation material derived from the autologous cells can be provided. This advantage is expected to radically dissolve the problem of clinically important rejection.

As the oral mucosal epithelial cells, cells existing in the dental root part (oral crevicular mucosal epithelial cells), cells of labial part, cells of palate part, cells of buccal part, and the like, can be used. Among them, it is particularly preferable to use oral crevicular mucosal epithelial cells because of the high proliferation ability and low antigenicity. The oral mucosal epithelial cells can be collected by ablating a site where target cells exist with the use of a scalpel, or by scraping it out. Oral crevicular mucosal epithelial cells can be collected by separating the oral mucosal epithelium that is attached to an extracted tooth from the enamel cement transition portion and collecting the cells from the oral mucosal epithelium. Note here that in order to remove impurities such as connective tissue, preferably, a treatment with enzyme such as dispase or trypsin, etc., filtration treatment are carried out.

Oral mucosal epithelial cells collected from a person other than the patient who is intended to undergo a transplantation of the sheet-shaped composition of the present invention can be used. However, taken immunorejection into consideration, it is preferable that oral mucosal epithelial cells are collected from the oral cavity of the patient and used for culture.

The oral mucosa has high proliferation potency. In the oral mucosa, generally, since the injury is cured after the operation by administering internal antimicrobial drug and carrying out disinfection with Iodine, and the like, for several days, the invasion with respect to the patient who was subjected to collection of mucosa seems to be light.

On the other hand, as the second cells, another individual's (allo) corneal epithelial cells can be preferably used. As such corneal epithelial cells, cells from donor's eyeball free from infection are available from, for example, eye bank (Northwest eye bank, etc.). The cells that can be used as the second cell are not limited to the corneal epithelial cells. Conjunctival epithelial cells, amnion epithelial cell, and the like, may be used. However, when the corneal epithelial cells constituting the corneal epithelium in a living organism or the conjunctival epithelial cells existing in the vicinity thereof are employed, it is thought that a sheet-shaped composition capable of reproducing the property of the corneal epithelium more excellently. As a result of the present inventor's investigation, when the corneal epithelial cells are used as the second cell, it was confirmed that a cell layer similar to the corneal epithelium was constructed. This fact supports the above-mentioned prediction and supports that the corneal epithelial cells are particularly preferable for the second cells. On the other hand, it was confirmed that when the amnion epithelial cells were used as the second cell, a cell layer capable of excellently reproducing the properties required for the cornea was formed. This fact shows that the amnion epithelial cells can be also preferably used as the second cells.

Autologous cells can be used as the second cells. However, when other individuals' cells are used, the cells can be obtained more easily. For example, even when a sheet-shaped composition for the treatment of a patient with bilateral eye disease is produced, the corneal epithelial cells as the second cells are available.

The separately prepared first cells and the second cells (hereinafter, also referred to as "the first cells, and the like") are seeded on amnion and cultured. In general, the first cells and the second cells, which are prepared in a form of a cell suspending solution, are dripped on amnion and cultured.

Typically, the seeding of the first cells and the seeding of the second cells are carried out simultaneously (herein, "simultaneously" includes not only a case where the seeding is carried out literally simultaneously but also a case where the first seeding is carried out and then the second seeding is carried out without substantial time interval). The first and second cells may be seeded at different timing. For example, the second cells may be seeded several minutes to several hours after the first cells are seeded. Such a time lag in seeding enables, for example, to construct non-uniform cell layer such as cell layer having those regions which are rich in cells derived from the first cells are localized.

The ratio of the first cells and the second cells to be seeded is not particularly limited. Typically, substantially the same number of the first and second cells are seeded. In an experiment in which the oral mucosal epithelial cells were used as the first cells and the corneal epithelial cells were used as the second cells, the ratio of the number of the first cells: second cells were changed to 3:7, 5:5, and 7:3 and comparison was carried out. As a result, no difference in terms of the cell proliferation and stratification were clearly observed among them (data not shown).

When the first and second cells are cultured on amnion, these cells are proliferated and a cell layer is formed (in this process, at least a part of the cells are thought to be differentiated). After the formation of a cell layer, a step of bringing the surface layer of the cell layer into contact with the air is carried out. This step is also referred to as air lifting in this specification. This step is carried out for differentiation of cells forming a cell layer and inducing the barrier function.

This step can be carried out by lowering the surface of the culture medium by temporarily removing a part of the culture medium by using a dropper, a pipette, and the like, thereby temporarily exposing the outermost layer of the cell layer to the outside of the culture medium. Alternatively, this step can be carried out by lifting up the cell layer together with the amnion, thereby temporarily exposing the outermost layer from the culture medium surface. Furthermore, by using the tube etc., the air may be fed into the culture medium so as to bring the uppermost layer of the cell layer into contact with the air. From the viewpoint of the ease in operation, it is preferable that by lowering the surface of the culture medium, thereby exposing the outermost layer of the cell layer to the outside.

The duration for carrying out this step, that is, the period of time when the uppermost layer of the cell layer is brought into contact with the air differs depending upon the state of the cells, culture conditions, and the like, but the duration may be, for example, three days to two weeks, preferably within a week, and further preferably within three days.

According to the above-mentioned method of the present invention, on the amnion, a corneal epithelium-like cell layer, in which the first cells and the second cells are stratified, is formed. The thus obtained sheet-shaped composition together with the amnion used as a substrate of the first cells and the second cells can be used as a transplantation material (substitute for the corneal epithelium) for patients with injured or defective cornea. In this case, the sheet-shaped composition is transplanted to the corneal epithelium defective part so that the amnion is located to the side of the eyeball.

In one embodiment of the present invention, cells of biological origin are cultured in the presence of support cells. The support cell is also referred to as a feeder cell and supplies a culture medium with a growth factor, etc. When the cells of biological origin are cultured in the coexistence of the support cells, the proliferation efficiency of cells is improved. As the support cell, for example, a 3T3 cell (Swiss mouse 3T3 cell, mouse NIH3T3 cell, 3T3J2 cell, etc.) and the like, may be used. Among them, it is preferable to use a mouse NIH3T3 cell as a support cell from the viewpoint of proliferation efficiency, ease in handling, etc.

It is preferable that the support cells are inactivated by using mitomycin C, etc. This is advantageous because the inhibition of the proliferation of the cells of biological origin due to the proliferation of the support cells themselves is prevented, and the proliferation efficiency of the cells of biological origin is enhanced. Such inactivation can be carried out by a radiation treatment, and the like.

The cell density of the support cells may be, for example, about $1\times10^2$ cells/cm$^2$ or more, preferably in the range from about $1\times10^2$ cells/cm$^2$ to about $1\times10^7$ cells/cm$^2$, and further preferably in the range from about $1\times10^3$ cells/cm$^2$ to about $1\times10^5$ cells/cm$^2$. As to the ratio with respect to the number of the first cells and the second cells, culture may be carried out under the conditions in which the number of the support cells to be used may be, for example, $1/10^3$ times to $1\times10^2$ times, and preferably $1/10^2$ times to 1 time as the total number of cells or biological origin. When the number of the support cells is small, the proliferation rate of the first cells and the like is lowered; and when it is too small, excellent proliferation and stratification of cells of biological origin cannot be obtained. On the other hand, it is not preferable that the number of the support cells is too large, because the proliferation rate of the oral mucosal epithelial cells is lowered.

When the cells of biological origin are cultured in the coexistence of support cells, it is preferable that an isolation membrane having a pore size to which the support cells cannot pass is provided between the support cells and the amnion. The use of the isolation membrane makes it possible to prevent the support cells from entering the side of the amnion (i.e. the side of living organism cells) at the time of culturing. As a result, the support cells may not be mixed in the finally obtained sheet-shaped composition. This means that a sheet-shaped composition being free from problem of immunological rejection by the support cells can be constructed. Clinically, this is extremely significant.

As the isolation membrane, an isolation membrane having a pore size through which the support cells cannot pass can be used by appropriately selecting the known membrane: For example, a polycarbonate membrane having a pore size of about 0.4 µm to 3.0 µm can be used. A material of the isolation membrane is not particularly limited. In addition to polycarbonate, polyester and the like may be used. Such isolation membranes are on the market and easily available.

Example of the culture method using an isolation membrane include the following method. Firstly, inactivated support cells are seeded and cultured on a container such as a dish (a first container), thereby forming a layer of support cells on the surface of the container. Next, a second container, which has a bottom face made of an isolation membrane, is set in the first container so that the bottom face of the second container is located in a culture medium. Then, the amnion is formed on the bottom face, that is, on the isolation membrane. Then, on the collagen layer, the cells of biological origin are seeded and cultured.

In one example, on bottom surface of the second container, amnion is previously formed (for example, on the bottom surface of the second container, the amnion from which an epithelium has been removed is placed. In this state, drying process is carried out). This second container is set in the first container in which support cells are seeded, and then on the collagen layer, the first cells and the like may be seeded and cultured.

The culture medium used for culturing the cells of biological origin is not particularly limited as long as the cells can be proliferated and stratified. For example, a culture medium, in which DMEM (Dulbecco's modified Eagle's medium) that is generally used for growing epithelial cells and Ham's F12 medium are mixed with each other at the predetermined ratio, and FBS, growth factor, antibiotics, and the like are added, may be used. Specific examples include a mixed culture medium of DMEM and Ham's F12 medium (mixing volume ratio of 1:1) to which FBS (10%), insulin (5 mg/ml), cholera toxin (0.1 nM), epithelial cell growth factor (EGF) (10 ng/ml) and penicillin-streptomycin (50 IU/ml) are added. Furthermore, a mixed culture medium of DMEM and Ham's F12 medium to which triiodothyronine (for example, 2 nM), glutamine (for example, 4 mM), transferrin (for example, 5 mg/ml), adenine (for example, 0.18 mM), and/or hydrocortisone (for example, 0.4 mg/ml) are further added, may be used.

The cells of biological origin may be cultured in the absence of xenogeneic cells. The "the absence of xenogeneic cells" in the present invention means that cells of animals different from the cells of biological origin are not used as a condition for culturing the cells of biological origin. Specifically, when human cells (for example, human skin epidermal cells or human corneal epithelial cells) are used, the condition means that cells from the animal species other than human, for example, a mouse, a rat, or the like, are not present (do not coexist). When cells are cultured in such a condition, xenogeneic components (including xenogeneic cells themselves) may not be contaminated in the finally obtained transplantation material (that is, sheet-shaped composition).

The culture medium used for culturing cells of biological origin is not particularly limited as long as it allows the cells to proliferate. For example, an MCDB153 medium (NISSUI PHARMACEUTICAL CO., LTD.), EpiLife™ (Cascade), and media produced by modifying the amino acid composition, etc. of these media, a culture medium mixing DMEM (Dulbecco's modified Eagle's medium) and Ham's F12 medium, which are usually used for growing epithelial cells, at a predetermined ratio can be used. In particular, in the present invention, it is preferable that a culture medium that does not contain serum and xenogeneic proteins is used. On the other hand, a culture medium containing growth factor, antibiotics, and the like may be used. However, it is preferable to use a culture medium that does not contain any serum. That is to say, it is preferable that serum free culture is employed as a culture method in the present invention. This is advantageous because problem such as immunological rejection due to the contamination of components derived from the serum can be avoided. Note here that culture may be carried out in a culture medium containing serum, in this case, however, it is preferable to use allogeneic serum (when cells of human origin is used, serum of human origin) or to use autologous serum. Needless to say, if possible, it is preferable to use autologous serum capable of avoiding causing the immunorejection.

The culture conditions may be changed in the course of culture for the purpose of excellently proliferating cells of biological origin.

As a result of the culturing step, cells of biological origin proliferate on the amnion. When the surface layer of the thus obtained cell layer is required to be keratinized (for example, a case where epidermal cells are used so as to form a skin epidermal sheet or a case where corneal epithelial cells are used so as to form a corneal epithelial sheet), the above-mentioned Air-lifting may be carried out.

The cells of biological origin are seeded on the amnion so that, for example, the cell density becomes about $1\times10^3$ cells/cm$^2$ or more, preferably in the range from about $1\times10^3$ cells/cm$^2$ to about $1\times10^7$ cells/cm$^2$, and further preferably in the range from about $1\times10^4$ cells/cm$^2$ to about $1\times10^6$ cells/cm$^2$.

In one preferable embodiment, amnion is placed on a collagen matrix containing human fibroblasts, which has been previously prepared, and then the cells of biological origin are seeded on the amnion and cultured. That is to say, in this embodiment, a step of culturing human fibroblasts in a collagen gel (the step B) and a step of placing amnion on the collagen gel, followed by seeding or placing cells of biological origin on the amnion (the step C) are carried out. The sheet-shaped composition that has been produced by this procedure has come to contain the cells of biological origin proliferated on the amnion placed on the collagen gel containing human fibroblasts. The sheet-shaped composition of this embodiment can be also used as a transplantation material after the collagen matrix is removed. Alternatively, the sheet-shaped composition of this embodiment can be also used as a transplantation material in a state in which it includes the collagen matrix.

"Collagen gel" functions as a culture substrate of human fibroblasts. The types of collagens as a material of the collagen gel are not particularly limited, and type I collagen, type III collagen, and type IV collagen, and the like, can be used. A plurality of collagens can be used in combination thereof. Such collagens can be extracted and purified from the connective tissue of the skin and cartilage, etc. of animals such as pig, bovine, sheep, etc., by an acid solubilization method, an alkali solubilization method, and an oxygen solubilization method, and the like. For the purpose of deteriorating the antigenicity, it is preferable to use so-called atherocollagen obtained by removing telopeptide by a treatment with the use of catabolic enzyme such as pepsin, trypsin, etc. As materials of the collagen gel, a collagen derived from amnion, particularly derived from human amnion may be used. Herein, the collagen layer is "derived from amnion" means that the collagen gel is obtained by using amnion as a starting material.

The origin of the human fibroblasts contained in the collagen gel is not particularly limited and it may be derived from any tissue as long as the tissue produces collagen. Human fibroblasts prepared from, for example, skin tissue, oral mucosa tissue, and the like, can be used.

A specific example of the method of producing a collagen matrix is shown. Firstly, human fibroblasts are prepared by the following procedure. The skin is collected, and then dermis is peeled off from the skin. The dermis is cut in strips and is brought into close contact with a dish coated with type I collagen. After static culture, human fibroblasts migrated from the dermis strip are subcultured. Cells are peeled off from the bottom surface of the dish and a cell suspending solution is prepared. The cell suspending solution is seeded on a cell culture dish. Appropriately, cells are cryopreserved (for example, stored in liquid nitrogen).

Meanwhile, a neutralized collagen solution is prepared by using type I collagen (see the below-mentioned Example). This is added in a culture container (for example, a culture insert) and stood still for ten minutes at room temperature so as to be gelled. Next, human fibroblasts in a logarithmic growth phase, which has been cultured by the above-mentioned method in advance, are mixed with this gel and gelled again. Thereafter, static culture is carried out. A collagen matrix containing human fibroblasts can be obtained by the above-mentioned procedure. This inventiveness allows the collagen matrix to have necessary strength and to have amnion layer or cells of biological origin to be mounted thereon, which makes a base of the present invention. A separately prepared amnion can be placed on (brought into contact with) the collagen matrix. Thereafter, cells are seeded and cultured in accordance with the above-mentioned procedure.

If the process of attaching adhesive components (fibrinogen, etc.) to the amniotic surface is performed, the formation of cell layer precedes the attachment of adhesive components. In order words, in this embodiment, cell layer is formed on the amnion, and then fibrinogen and any other adhesive components are attached to the amniotic surface (surface where no cell layer is formed).

EXAMPLE 1

1. Trehalose Treatment/Preparation of Lyophilized Amnion 1-1. Harvesting of Amnion A sufficient informed consent was obtained in advance from a pregnant woman who had no systemic complications but was undergoing a caesarian operation, in the presence of an obstetrician. An amnion was obtained from the woman during the caesarian operation in operation room. The operation was performed with cleanness being ensured, and with a dedicated garment worn after scrubbing according the surgical procedure. Before delivery, a clean vat for harvesting amnion and physiological saline for washing were prepared. After delivery, placental tissue was transferred to the vat and amniotic tissue was manually detached from the placenta. Any adhesion between the amnion and placenta was cut off using a scissor.

1-2. Treatment of Amnion

Treatment of amnion was performed in the order of (1) washing, (2) trimming, and (3) storage. In any of these steps, the procedure was preferably performed under a draft, the container and instruments that were used had been previously sterilized, and disposable type of dish, etc were used. Blood components attached to the amnion obtained were washed off with physiological saline, and an additional sufficient amount of physiological saline (0.005% ofloxacin added) was used to wash further. Subsequently, phosphate buffered saline (PBS) added with penicillin-streptomycin (50 IU) was used to wash three times in total. Then, the amnion was transferred to the dish, and cut into pieces of about 4×3 cm with scissors. After the cutting, amnions in a good condition were selected based on the shape and thickness.

1-3. Storage of Amnions 2 cc sterilized cryotubes received preservation solution 1 cc each, into which one piece each of harvested and washed amnion was put. The cryotubes were labeled and stored in at −80° C. in a deep freezer. As the preservation solution, solution of 50% sterilized glycerol in DMEM (Dulbecco'S Modified Eagle Medium: GIBCOBRL) was used. The duration for use of the preserved amnion was determined to be three months, and at the end of the duration, the cryotubes were burned and discarded. The described storage process can be done without, and the following epithelium treatment may be performed.

1-4. Treatment of Amniotic Epithelium

The amnion which had been stored at −80° C. was thawed in a room temperature, and was washed twice with phosphate buffered solution (PBS) added with penicillin-streptomycin (50 IU). The washed amnion was immersed in 0.02% EDTA solution (Nacalai tesque) (100 mm dish), and reacted in a $CO_2$ incubator at 37° C. for one hour. After the reaction, the amnion was washed twice with a sufficient amount of PBS, and had its epithelium manually peeled off (removed) using cell scraper (Nunc, USA) under stereoscopic microscope. Complete removal by peeling-off of additional amniotic epithelium by the process was ensured by inspection under light microscope and electron microscope (electron microscope scanning).

1-5. Treatment by Trehalose/Production of Lyophilized Amnion

The amnion with an epithelium removed is immersed in 10% (w/v) trehalose solution at 37° C. for two hours. The trehalose solution was prepared by diluting trehalose (Torehainochi, H plus V Lifescience, Hayashibara) with distilled water. pH of the solution was maintained in the rage of 7 through 10. The amnion was clamped with a pair of sterilized plastic frames, and secured with clip. Each set of the frame was transferred into a deep freezer at −80° C., and, upon determination of freezing of the amnion, lyophilization process (−110° C., about one hour) was performed using a vacuum lyophilizer (Yamato, NEOCOOL). Conditions were set according to the instruction from the manufacturer such that sufficiently desiccated products can be obtained. The amnion after the lyophilization process was released from the frame, transferred into a two-layered bag made of polyamide-nylon on the outside and polyethylene on the inside, and packed in vacuum using a vacuum packer for home use (Framenova, Magicpack). The amnion packed in vacuum was irradiated with γ-ray (about 25 kGy) to sterilize it. The sterilized amnion was stored in the vacuum package at a normal temperature until immediately before use. The state immediately after the lyophilization process was still maintained even 12 months after start of the storage. Further experiments were performed using the desiccated amnion which was stored at a normal temperature for one month.

2. Treatment with Trehalose/Evaluation of Physical Properties of Lyophilized Amnion Trehalose-treated and lyophilized amnion (also referred to as trehalose-treated FD-AM) prepared in the above procedure was immersed in PBS at a room temperature until its sufficient recovery, and its physical properties evaluated. Tested items and method is as follows. The material used for the test was five pieces of trehalose-treated and lyophilized amnion which had been separately prepared. An average of the measurements obtained was used for the evaluation. Additionally, those amnion (raw amnion) which had not underwent none of epithelial treatment, trehalose-treatment and lyophilization and those amnion which had been prepared through similar procedures except the trehalose treatment were prepared, and served as a standard (control for comparison) in the evaluation of physical properties.
(1) (Thickness)
Measurement of the thickness was performed using a Double Scan High-accuracy laser meter (LT-9010M) from Keyence.
(2) (Transparency)
Tubidimeter (NDH2000) from Nihon-Denshoku was used to measure the haze for use in evaluation of transparency. Haze is calculated according to the following equation:

Haze=Diffused Transmission Factor (DF)/Total Light Transmittance (TT)

(3) Tensile Strength
Tensile strength meter (Tensilon RTC-1210A) from A&D was used for measurement of tensile strength.
(4) Flexibility
Microscope for microsurgery from Karlzeiss was used for measuring flexibility by macroscopically detecting presence of wrinkles. The number of wrinkles on the entire eye ball surface was counted by three persons, and their average was used for evaluating flexibility.

Figure 3:
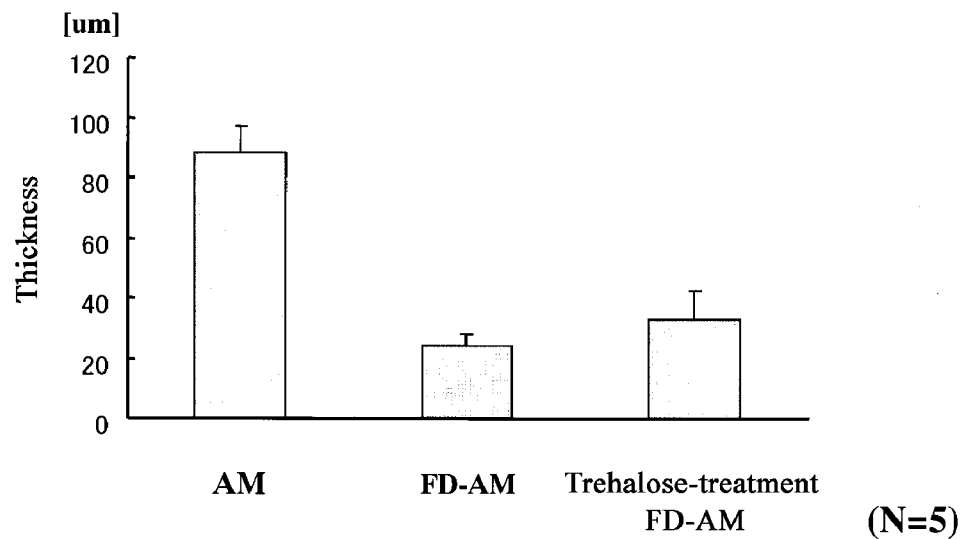
FIG. 3 is a graph showing the result of an evaluation test of physical properties (thickness) of the trehalose-treated and lyophilized amnion.

The test results are shown in FIG. 3 through 6. As shown in FIG. 3, trehalose-treated and lyophilized amnion is found to be thicker than lyophilized amnion. This is thought to be due to a higher water retention capacity afforded by the trehalose treatment. Removal of epithelium is reflected upon the significantly reduced thickness of the trehalose-treated and lyophilized amnion compared to raw amnion (AM).

Figure 4:
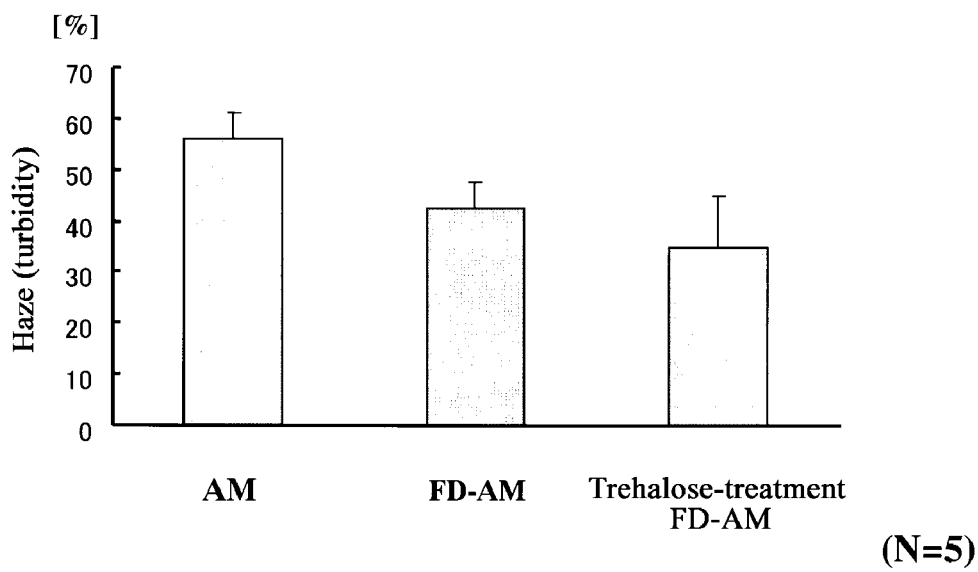
FIG. 4 is a graph showing the result of an evaluation test of physical properties (clarity) of the trehalose-treated and lyophilized amnion.

It is also noted that, as shown in FIG. 4, trehalose-treated and lyophilized amnion has a higher transparency than lyophilized amnion. Surprisingly, it was revealed that trehalose treatment enhances transparency. The poorer transparency of the raw amnion compared to the trehalose-treated and lyophilized amnion is due to the presence of epithelium.

Figure 5:
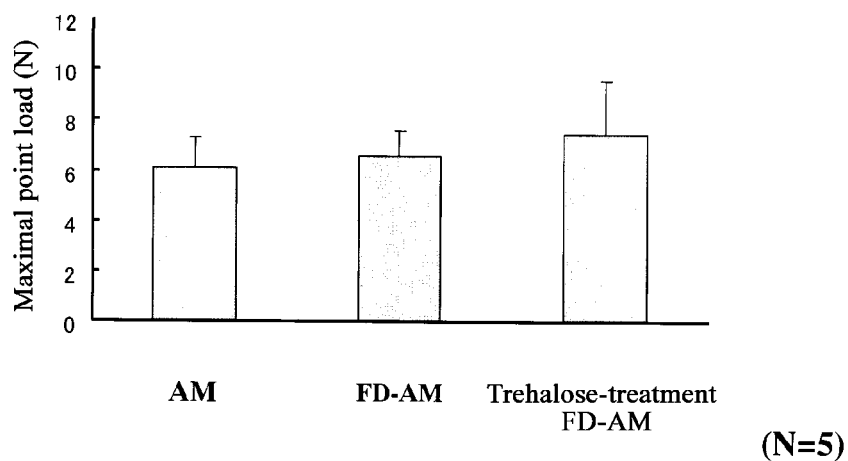
FIG. 5 is a graph showing the result of an evaluation test of physical properties (tensile strength) of the trehalose-treated and lyophilized amnion.

On the other hand, as shown in FIG. 5, trehalose-treated and lyophilized amnion has a higher tensile strength than lyophilized amnion. Surprisingly, the trehalose-treated and lyophilized amnion has a higher strength even compared amnion comprising an epithelium (raw amnion). Thus, it was revealed that trehalose treatment is extremely effective in enhancing the strength of amnion.

Figure 6:
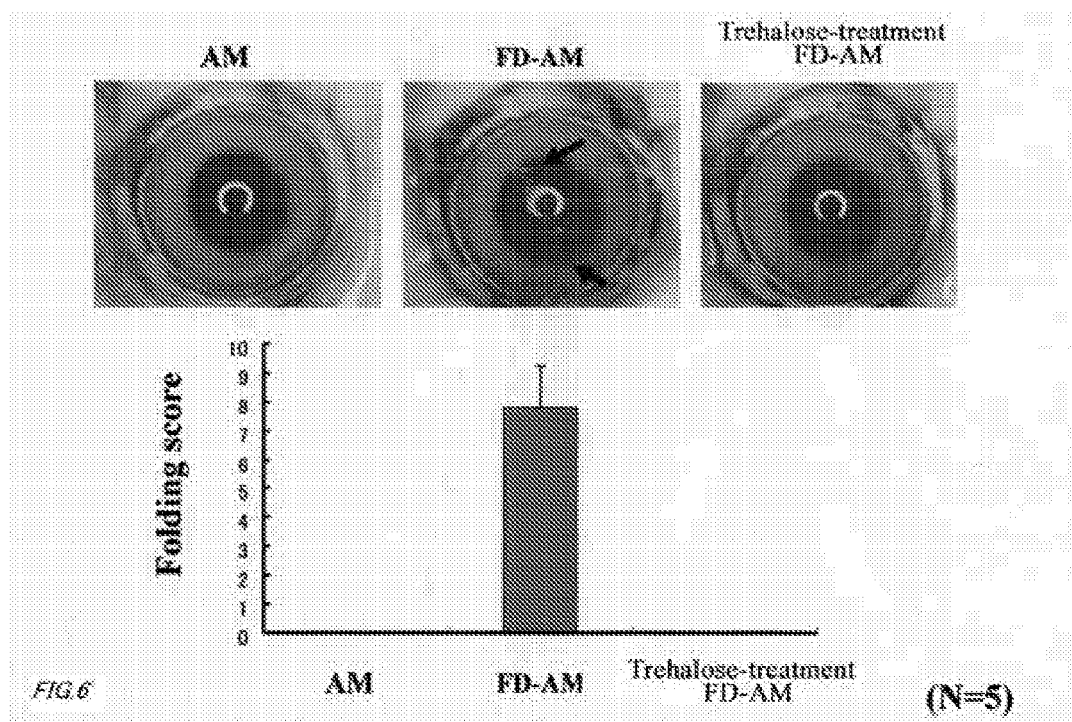
FIG. 6 is a graph showing the result of an evaluation test of physical properties (flexibility) of the trehalose-treated and lyophilized amnion.

Further, as shown in FIG. 6, the flexibility of trehalose-treated and lyophilized amnion is far from that of lyophilized amnion, but is equivalent to that of raw amnion. Thus, it was revealed that trehalose treatment is extremely effective in enhancing flexibility of amnion.

3. Evaluation of Biocompatibility of Trehalose-Treated and Lyophilized Amnion

Materials that are transplanted into an organism are required to have a high biocompatibility. Therefore, the biocompatibility of trehalose-treated and lyophilized amnion was evaluated by the following procedure.

Figure 7:
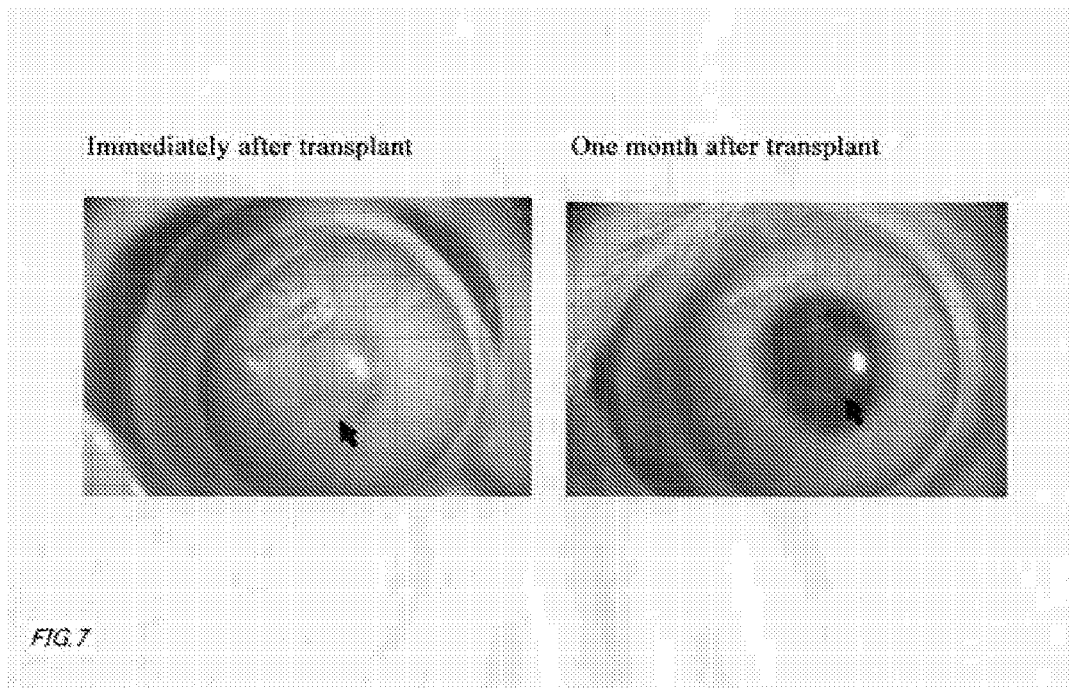
FIG. 7 is a pair of photographs showing the result of an evaluation test of biocompatibility of the trehalose-treated and lyophilized amnion. The trehalose-treated and lyophilized amnion was transplanted to between rabbit corneal parenchyma layers, and the state of its eye surface was monitored. The left photograph in the left shows the state of eye surface immediately after the transplant, and that in the right side shows the state of eye surface 1 month after the transplant.

6 week old Japanese rabbit received an incision with a scalpel on its eye surface into parenchymal layer of cornea. Subsequently, an appropriately sized trehalose-treated and lyophilized amnion was inserted into the incision of parenchymal layer. After the transplant, the state of the eye surface was monitored for a period of time. The states of the eye surface immediately after and one month post the transplant are shown in FIG. 7. At one month after the transplant, no angiogenesis occurring from surrounding area as well as inflammation reaction were recognized. The transparency of the eye surface was greatly enhanced compared to that immediately after the transplant. Thus, it was determined that the biocompatibility of trehalose-treated and lyophilized amnion is equivalent to that of untreated amnion.

Figure 8:
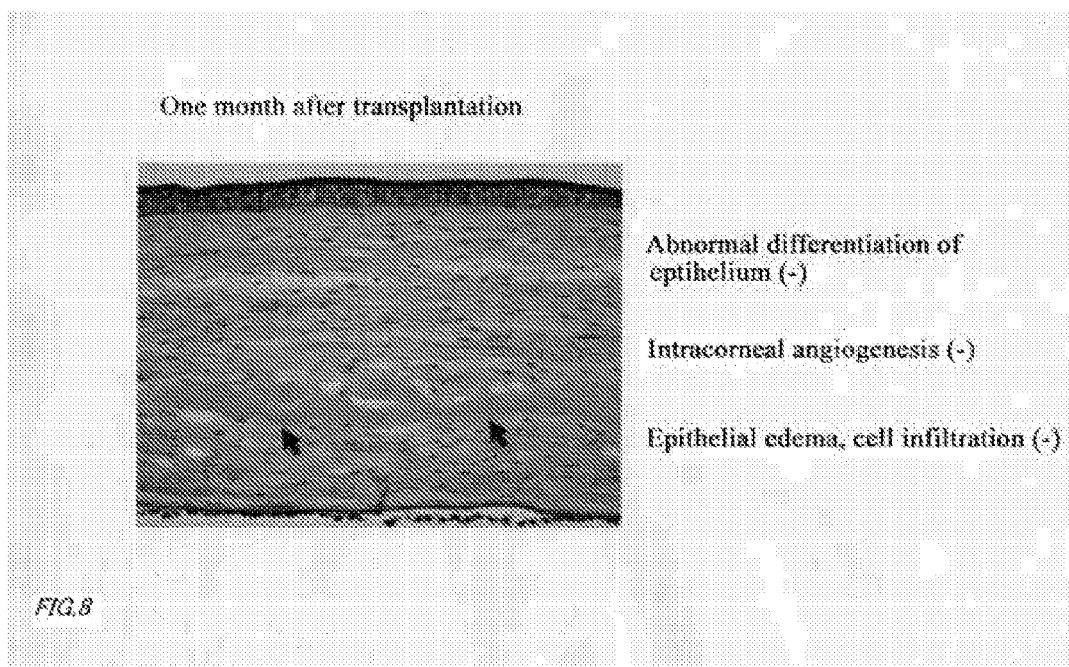
FIG. 8 is a photograph showing the result of an evaluation test of biocompatibility of the trehalose-treated and lyophilized amnion. The trehalose-treated and lyophilized amnion was transplanted to between rabbit corneal parenchyma layers, and a part of the cornea including the transplanted region was isolated and subjected to HE staining at 1 month after the transplant.

In order to examine the biocompatibility in greater details, a part of the cornea including the transplanted portion was subjected to HE staining at one month post the transplant. Image of the HE staining is shown in FIG. 8. The graft (i.e. trehalose-treated and lyophilized amnion) is indicated with an arrow. As clearly shown in FIG. 8, none of abnormal differentiation, intracorneal angiogenesis, edema, and cellular infiltration is recognized in the epithelium. Consequently, it was demonstrated that trehalose-treated and lyophilized amnion has an extremely low antigenicity, and is therefore superior in biocompatibility.

4. Production of Cultured Corneal Epithelial Sheet Using Trehalose-Treated and Lyophilized Amnion 4-1. Recovery of Corneal Epithelial Cells
Corneal harvested from 6 week old Japanese white rabbit was immersed in DMEM containing 10% fetal bovine serum (FBS), and had its conjunctiva, corneal endothelium and other unnecessary tissue excised. Tissue was then washed with phosphate buffered solution (PBS) and immersed in phosphate buffered solution (PBS) containing 1.2 U/ml of dispase (Nacalai tesque) at 37° C. for one hour. The tissue after the treatment was taken out, and immersed in 0.02% EDTA at a room temperature for two minutes, and then in phosphate buffered solution at a room temperature for two minutes to arrest the dispase activity. Corneal epithelial cells were peeled off in DMEM containing 10% fetal bovine serum (FBS), and subjected to centrifugation to concentrate and recover the corneal epithelial cells.

4-2. Preparation of Cocultured Cells

NIH-3T3 cells (hereinafter, referred to simply as "3T3 cells") were used as cocultured cells (supporting cells). 3T3 cells previously cultured to confluent in 75F flask (BD Falcon) were immersed in 0.05% mitomycin C solution for two hours to suppress the proliferative activity of 3T3. Subsequently, the cells were washed several times with phosphate buffered solution (PBS) to remove mitomycin C. The cells were then treated with 0.05% trypsin-EDTA solution, and pippeted to provide a cell suspension (3T3 cell suspension).

4-3. Formation of Cell Layer

Trehalose-treated and lyophilized amnion obtained in 1 was immersed at a room temperature in PBS until sufficient recovery. The amnion prepared in this manner was used as substrate for co-culturing corneal epithelial cells and 3T3 cells according to the following procedure. As culture instruments, 6 well-culture dish (Corning, N.Y.) and culture insert (culture insert container) (made of polycarbonate, average pore size 3.0 µm, Corning, N.Y.) were used.

The culture dish was first seeded with 3T3 cell suspension to a cell density of about $1\times10^4$ cell/cm$^2$ and incubated at 37° C. under 5% $CO_2$. Meanwhile, amnion was attached on the culture insert, with its side of basal membrane (where the epithelium was present) facing upward, and dried at a room temperature for ten minutes. Then, the culture insert having the amnion attached was seeded with suspension of corneal epithelial cell to a cell density of about $1\times10^5$ cell/cm$^2$.

Figure 9:
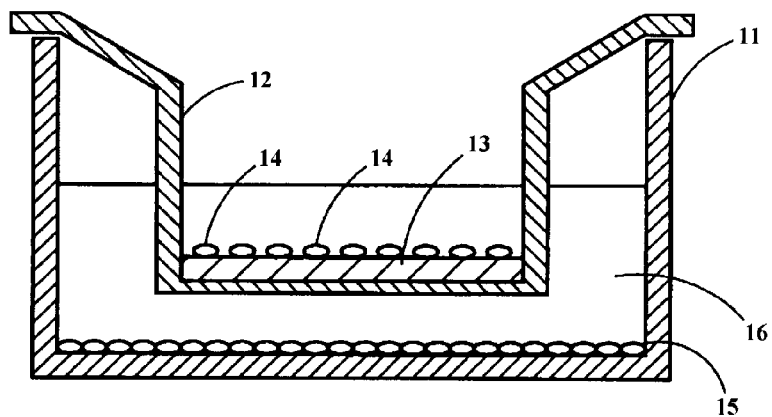
FIG. 9 is a sectional view schematically showing the state of instruments for culturing the corneal epithelial cells on the trehalose-treated lyophilized amnion. Culture insert 12 was stood still on culture dish 11, on the bottom surface of which is formed 3T3 cell layer 15. On the other hand, an amnion 13 was stood still on the bottom surface of the culture insert 12, to receive and culture corneal epithelial cells 14 thereon. Numeral 16 denotes the culture media.

Following the above procedure, the culture insert was placed inside the culture dish, as shown in FIG. 9, and 3T3 cells and corneal epithelial cells were cultured on the same culture media. FIG. 9 is a sectional schematically showing the state during the culture. Culture insert 12 stands still inside culture dish 11, on the bottom of which is formed 3T3 cell layer 15. On the bottom of culture insert 12 is amnion 13 standing still, on which corneal epithelial cells 14 are cultured. Numeral 16 represents culture media.

The media used was DMEM/ham F12 mixed media (mixed volume ratio 1:1) added with 10% FBS, insulin (5 mg/ml), cholera toxin (0.1 nM), penicillin streptomycin (50 IU/ml), human recombinant epithelial cell growth factor (EGF) (10 ng/ml).

3 week cultivation was performed in the above media (Submerge). Then, in order to induce differentiation of mucosal epithelium, so called "air-lifting" method was used to continue the cultivation for further one week. In the air-lifting method, the surface level of the media is brought to level with the corneal epithelial cell-derived cell layer formed on the amnion, while exposing the surface of the cell layer to the air. During the submerge process, the media was exchanged on every other day, and, after the air-lifting process, was exchanged daily to perform the cultivation. As result, cell layer was formed on the amnion.

5. Verification of Histological Properties of Cultured Corneal Epithelial Sheet

Figure 10:
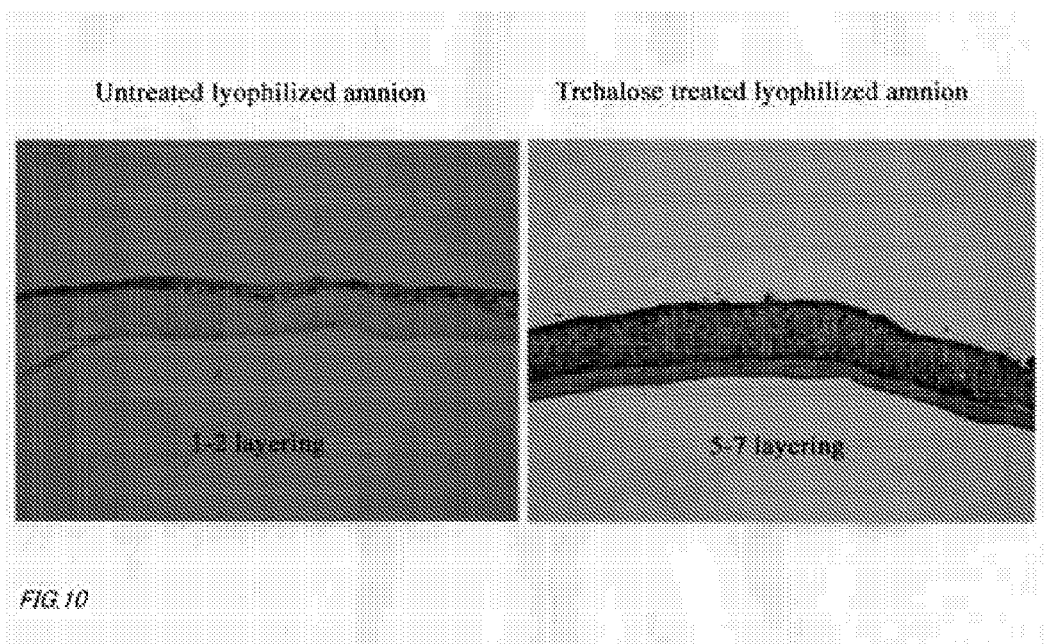
FIG. 10 is a pair of photographs (HE staining image) showing the cell layer formed on the trehalose-treated and lyophilized amnion. For comparison, the cell layer formed on the amnion after lyophilization but without the trehalose-treatment (Un-treated lyophilized amnion) is shown.

At 2 days of cultivation after the air-lifting, cell layer similar to corneal epithelium was formed (FIG. 10, right). It can be seen in the cell layer that cells are 5-7 layered in the same manner in normal corneal epithelium. Amniotic side of the cell layer had cells similar to basal cells in a relatively columnar shape. Those cells in outermost layer were flat and had nuclei while not keratinized on its surface unlike skin. Thus, it was ascertained that cell layer similar to corneal epithelium (corneal epithelium-like layer) was formed on the amnion.

On the other hand, when lyophilized amnion without trehalose treatment (lyophilized amnion) was used as substrate to similarly culture the corneal epithelial cells, formation of cell layer occurs only in a limited fashion, resulting in 1-2 layers (FIG. 10 left). Therefore, it can be determined that trehalose-treated and lyophilized amnion can exerts it function to facilitate a normal differentiation of cornea.

Subsequently, immuno-staining was performed to further investigate the histological properties of the cell layer. First, the cell layer obtained was cut together with the amnion into an appropriate size, frozen-embedded in OCT compound, and then sliced in cryostat to produce slide sections. The immuno-staining was targeted to keratin, representative cytoskeletal proteins. In particular, expressions of cornea-specific keratin 3, epidermis-specific keratin 10, and conjunctiva-specific keratin 13 were examined according to the following method. Slide section was washed with phosphate buffered solution (PBS) and blocked with 1% fetal bovine serum (FBS) to inhibit non-specific antibody reaction. Then, antibodies (first antibody) specific for each of the keratins were reacted at a room temperature for one hour. After the reaction, washing was performed in PBS containing Triton-X for 15 minutes three times, and fluorescence-labeled antibodies (second antibody) were reacted at a room temperature for one hour. After the reaction, washing was performed for 15 minutes three times in phosphate buffer solution (PBS), and, upon mounting, tissues were visualized under confocal microscope.

Figure 11:
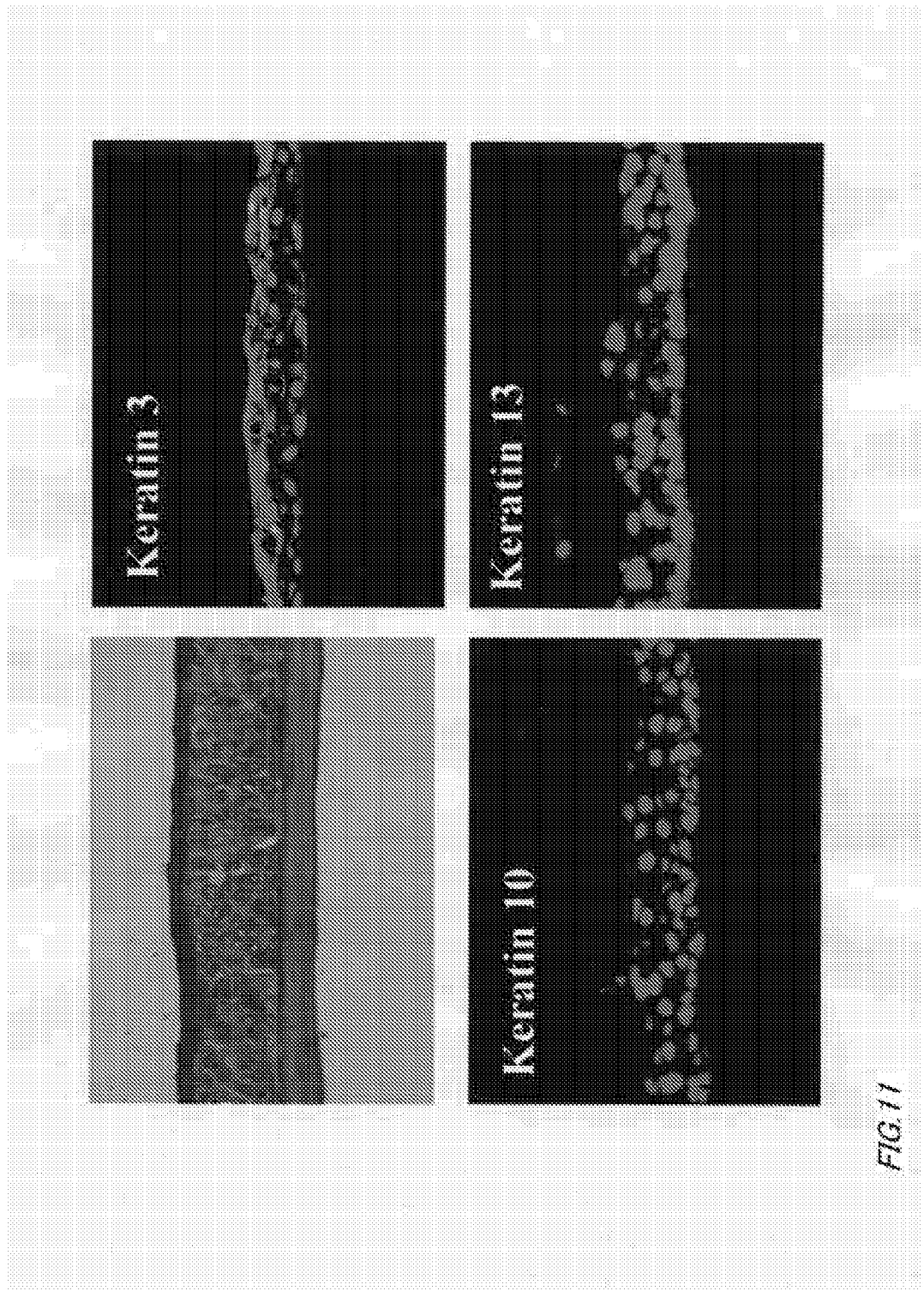
FIG. 11 is a series of photographs showing HE staining images and immuno-staining images of the sheet (cultured corneal epithelial sheet) with the cell layer formed on the trehalose-treated and lyophilized amnion. Signals for each antibody in the immuno-staining images are colored green. Cell nuclei are colored red. Corneal keratin is expressed (+), with the keratinized skin-type of keratin 10 (−) and corneal type of keratin 13 (−) not expressed.

The antibody reactions for each of the listed keratins in the cell layer were as follows. First, there were no staining for epidermis-specific keratin 10 and conjunctiva-specific keratin 13 evident (FIG. 11, lower). On the other hand, staining for cornea-specific keratin 3 was extensively evident (FIG. 11 upper right). The staining for keratin 3 was intense in upper portion of the cell layer. Based on these results, it was demonstrated that epithelial cell layer similar to normal corneal epithelium was formed.

6. Transplant Experiment Using Cultured Corneal Epithelium Sheet

The sheet produced in 4 which had corneal epithelium-like cell layer formed there (Cultured corneal epithelium sheet) was used to perform the following transplant experiment.

First, the rabbit from which corneal epithelial cells had been harvested received ablation with crescent knife to thoroughly remove the area spanning 4 mm from its limbus to corneal and conjunctival epithelium in a depth of 100 µm. Since this ablation eliminates epithelial cells including corneal epithelial stem cells, it is believed that artificial eye surface stem cell exhaustion is reproduced. Subsequently, cultured corneal epithelium sheet was transplanted to a region slightly inward from the limbus. 10-nylon thread was used for the transplant to perform the suture with surrounding tissues. After the transplant, therapeutic contact lens was sutured on the graft. Upon completion of the surgery, antibiotics and steroid eye lotion were applied twice a day. The eye surface after the transplant had a similar transparency to that of cultured corneal epithelium sheet prior to the transplant.

The eye surface that had undergone the transplant was visualized two days and 14 days after the transplant. At the same time, fluorescein staining test was performed by applying fluorescein test paper containing moisture such as amniotic eye drop directly onto eye surface, making the subject blink several times, and visualizing the fluorescein staining of the eye surface. If corneal epithelium remains, its intercellular adhesive structure prevents fluorescein dye from infiltrating, thereby producing no staining by fluorescein.

Figure 12:
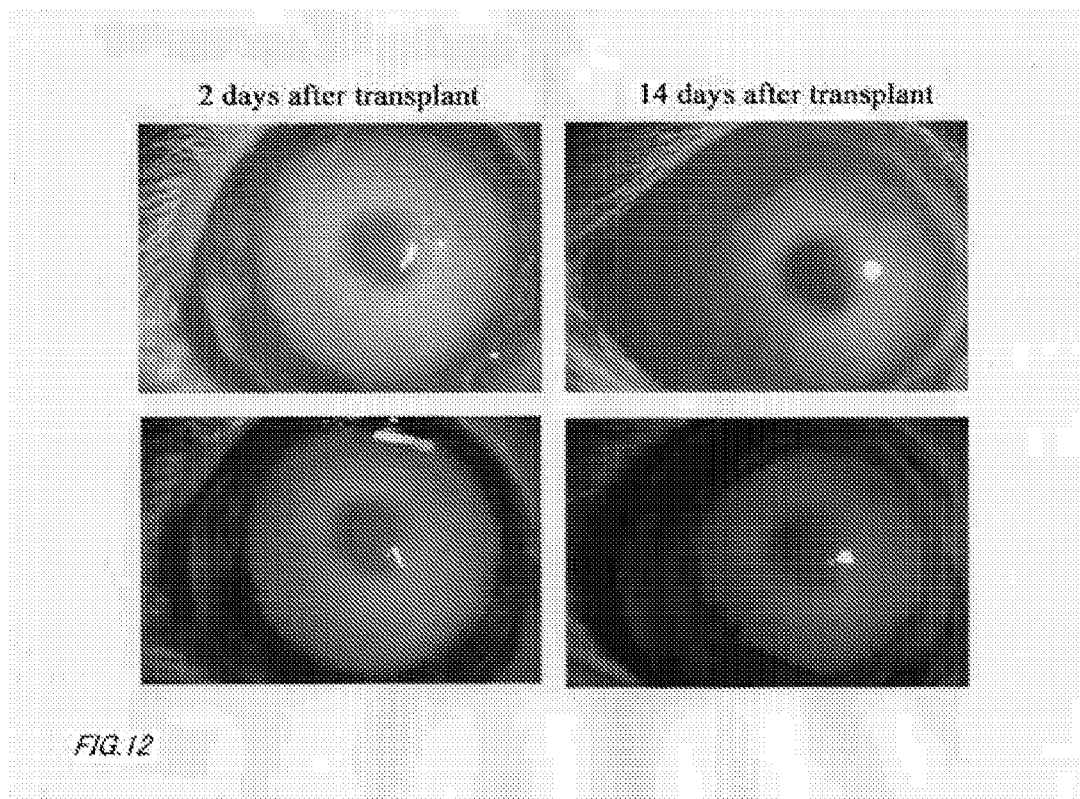
FIG. 12 is a series of photographs showing the reconstruction effect of the cultured corneal epithelial sheet made of the trehalose-treated and lyophilized amnion. The states of eye surface 2 days and 14 days after the cultured corneal epithelial sheet transplant (upper) and their fluorescein staining images (lower) are shown.

At two days after the transplant, the eye surface retained its transparency (FIG. 12, upper left). In addition, it was revealed by fluorescein staining that cultured corneal sheet remained on the eye surface without any defect (FIG. 12, lower left). On the other hand, based on the observation that transplanted cultured corneal epithelium sheet shows no fluorescein staining, it was demonstrated that cultured corneal epithelium sheet had a similar barrier function to that of corneal epithelium. Further, it was noted that fluorescein staining was evident all around the periphery of the transplanted cultured corneal epithelium sheet, thus demonstrating that those tissues which was present on the transplanted was not due to contamination by surrounding residual conjunctival epithelium.

Since cells in corneal epithelium typically bind to each other in a tight adhesive structure, fluorescein dye does not infiltrate the surface. Specifically, no staining is shown in fluorescein staining test. In contrast, when those cells had their adhesion loosened or had their barrier function disrupted due to detachment of cells themselves, infiltration of fluorescein dye is allowed to stain the tissue. Accordingly, by examining any staining by fluorescein dye, it can be determined whether or not transplanted cultured corneal epithelium sheet has a similar barrier function to that of corneal epithelium.

On the other hand, it was observed that at 14 days after transplant, the cultured corneal epithelial sheet still remained on the eye surface, and additionally, extended toward periphery compared the state at 2 days after the transplant, covering the entire eye surface (FIG. 12, upper right). Also, it was observed that the eye surface itself showed no fluorescein staining, indicating that the cultured corneal epithelium sheet retained its barrier function (FIG. 12 lower right). Transparency had no changes from that at 2 days after the transplant, and was retained at a high level (FIG. 12 upper right).

Based on the above results, it was demonstrated that cultured corneal epithelium sheet obtained by using trehalose-treated and lyophilized amnion as a substrate is provided with a favorable take to eye surface, which is maintained for an extended time period. Moreover, its was observed that the sheet extends to periphery after transplant to exert a barrier function required as corneal epithelium for an extended time period, while maintaining a high transparency. Specifically, it was observed that the cultured corneal epithelium sheet obtained according to the above method serves favorably as a substitute for corneal epithelium, and can be favorably used as a graft for reconstructing eye surface, for example in the event where any damage or defect has been caused on cornea.

Figure 13:
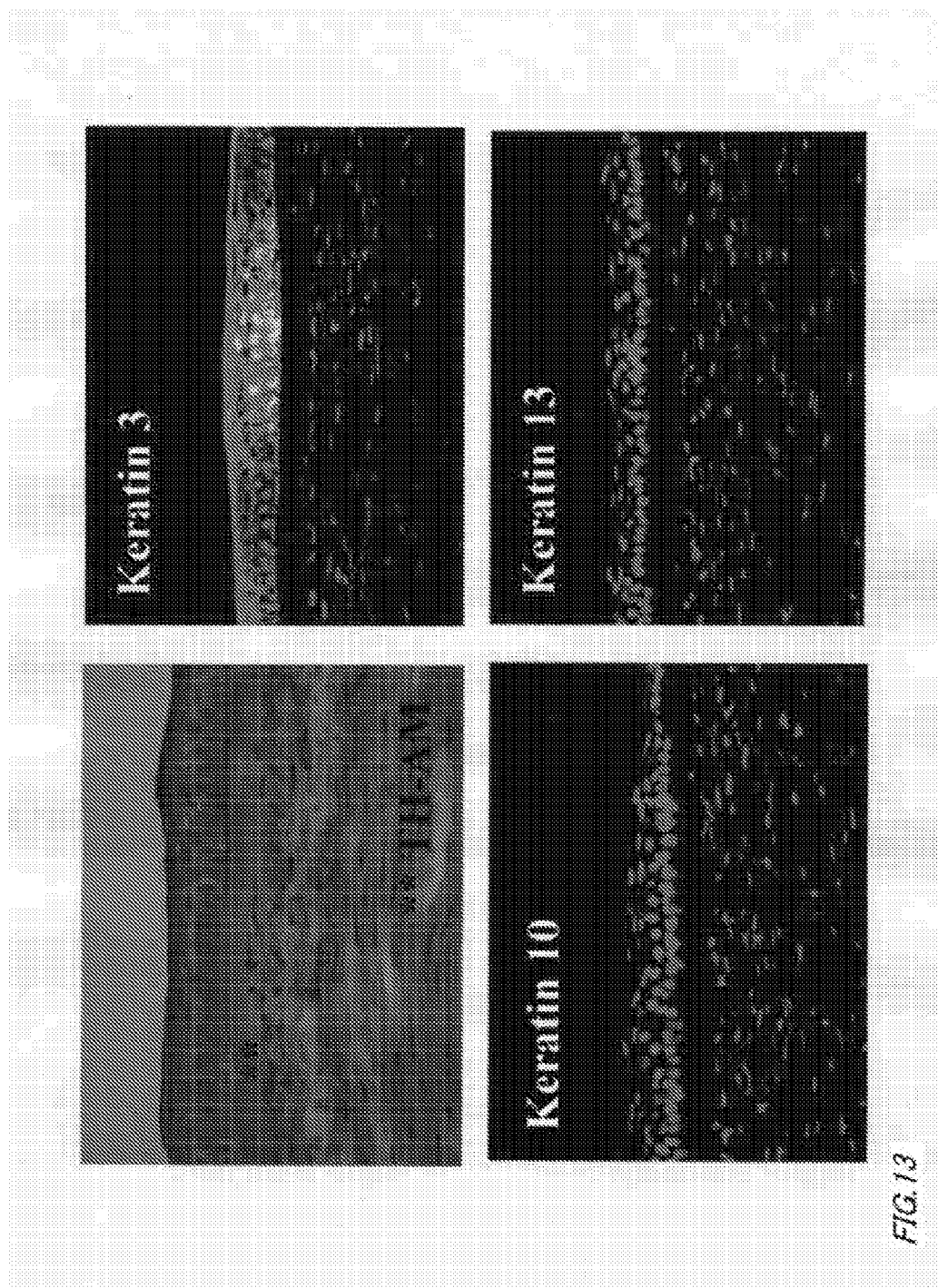
FIG. 13 is a series of photographs showing the HE staining images (upper left) and immuno-staining images (upper right and lower) for various keratins of the cultured corneal epithelial sheet 2 weeks after the transplant. Mark ** denotes trehalose-treated and lyophilized amnions (TH-AM).

7. Evaluation of Histological Properties of Transplanted Cultured Corneal Epithelium Sheet The cultured corneal epithelium sheet was removed two weeks after the transplant for inspection of its histological properties. FIG. 13 show in upper left image HE staining image of the cultured corneal epithelium sheet. Cell layer where cells are regularly arranged, similarly to that of normal corneal epithelium, can be found on trehalose-treated and lyophilized amnion (TH-AM, marked with **). In that image, the upper cell layer has many more flat cells, and maintains a structure extremely similar to that of corneal epithelium.

Results of staining test for each of the keratins are shown in upper right image and lower image of FIG. 13. Generally similar staining to those of cultured corneal epithelium sheet prior to the transplant was shown. Specifically, staining for the epidermis-specific keratin 10 and conjunctiva-specific keratin 13 were not evident (FIG. 13, lower), while staining for only corneal-specific keratin 3 was evident for the entire cell layer (FIG. 13, upper right). Thus, it was determined that the cultured corneal epithelium sheet, even after the transplant, maintained the corneal-specific keratin. This result supports from the histological view point that cultured corneal epithelial sheet exerts a similar function to corneal epithelium for an extended period of time.

8. Immuno-staining for Basal Membrane and Stratum Compactum Components

In order for amnion to favorably act as a substrate for cell culture, it is believed that the basal membrane and stratum compactum preferably have retained their innate structures. Whether or not the basal membrane and stratum compactum have retained their innate structures can be evaluated by examining the presence or absence (whether or not they are retained) of components characteristic of each of these. Thus, the following immuno-staining method was used to examine whether or not the basal membrane and stratum compactum components are retained in trehalose-treated and lyophilized amnion. In this method, amnion that had undergone none of epithelium process, trehalose treatment process and lyophilization process (raw amnion) and amnion that had been prepared in the same manner as trehalose-treated and lyophilized amnion except that it had not undergone trehalose treatment (lyophilized amnion) were compared.

First, each amnion was cut into a size of 1.5×1.5 cm, embedded in OCT compound, and frozen at −80° C. to provide frozen preparations. These preparations in the frozen state were sliced into a thickness of 8 μm in the vertical direction to amniotic surface in cryostat (CM1900 Leica), and mounted on glass slide to provide as frozen section. These sections were used in the immuno-staining according to the following procedure.

1. Acetone fixation, 5 min., 2. Washing in PBS, 30 min., 3. Blocking with PBS/3% BSA 15 min., 4. First antibody, one hour, 5. Washing in PBS, 30 min. 6. Blocking with PBS/3% BSA, 15 min., 7. Second antibody, one hour, 8. Washing in PBS, 30 min., and 9. Mounting.

Samples after mounting were visualized under fluorescence microscope (Leica DMIRB).

Antibodies that were used are as follows. Dosages were determined according to the instruction from the manufacturers.

Collagen I (Collagen I): LSL LB-1190, Collagen III (Collagen III): LSL LB1300, Collagen IV (Collagen IV): LSL LB-1407, CollagenV (Collagen V): LSL LB1581, Collagen VII (Collagen VII): Chemicon MAB1345, Laminin 5 (Laminin-5): Chemicon MAB19562, Fibronectin (Fibronectin): LSL LB-1021.

Amniotic basal membrane layer has expressions of Collagen IV, VII and Laminin 5, while stratum compactum layer has expressions of Collagen I, III, V, and Fibronectin. Therefore, immuno-staining using antibodies for each of these allows for visualization of any amniotic basal membrane and stratum compactum that were retained. In addition, since PI staining is also performed in the instant experiment, the presence or absence of amniotic epithelial cells can be simultaneously determined.

Figure 14:
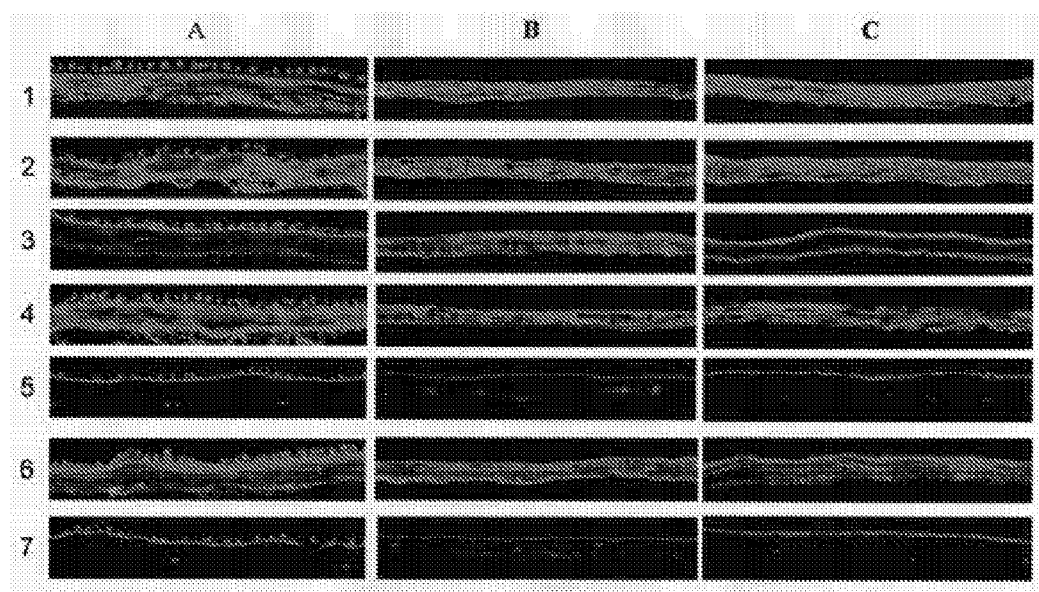
FIG. 14 is a series of photographs showing the results of immuno-staining of the trehalose-treated and lyophilized amnions using an antibody directed against a basal membrane specific component and an antibody directed against a stratum compactum specific component. The immuno-staining images (C) of the trehalose-treated and lyophilized amnion are shown in comparison to those of raw amnions (A) and of lyophilized amnion without the trehalose-treatment (B). 1; Staining images of Collagen I, 2; Staining images of Collagen III, 3; Staining images of Collagen IV, 4; Staining images of Collagen V, 5; Staining images of Collagen VII, 6; Staining images of laminin 5, and 7; Staining images of Fibronectin.

Results of the immuno-staining are shown in FIG. 14. Images in column A are staining images of raw amnions, those in column B are staining images of lyophilized amnions, and those in column C are staining images of trehalose-treated and lyophilized amnions. The images in each column are, in the order from the uppermost one to the lowermost one, (1) staining images of Collagen I, (2) staining images of Collagen III, (3) staining images of Collagen IV, (4) staining images of Collagen V, (5) staining images of Collagen VII, (6) staining images of Laminin 5, and (7) staining images of Fibronectin.

The following facts were revealed as result of the staining. First, compared to lyophilized amnion, trehalose-treated and lyophilized amnion had stronger signals for basal membrane components (Collagen IV, Collagen VII, Laminin 5), showing the staining for basal membrane components that is similar to that of raw amnion. This indicates that trehalose-treated and lyophilized amnion highly maintains its innate structure of the basal membrane. In a part (Collage IV and Fibronectin) of the staining results, staining was evident on the entire lyophilized amnion, while trehalose treated and lyophilized amnion had relatively clear confines of stained region and non-stained region, similarly to raw amnion. This indicates that trehalose treated and lyophilized amnion highly retains its innate structures basal membrane and stratum compactum.

As can be apparently shown in the staining result of the stratum compactum, trehalose-treated and lyophilized amnion has stratum compactum that is thicker than that of lyophilized amnion. It was revealed that, when returned to a moistened state, a favorable swell of stratum compactum as well as recovery of thickness to a similar level to that of raw amnion resulted from the trehalose treatment.

Thus, it was thus revealed that trehalose treated and lyophilized amnion has structures of basal membrane and stratum compactum that are similar to those of raw amnion. Specifically, it was ascertained that trehalose treatment prevents the structures of basal membrane and stratum compactum from being damaged during lyophilization, thereby providing amnion with structures of basal membrane and stratum compactum that are similar to raw amnion.

9. Review of Method for Removing Epithelium

Figure 15:
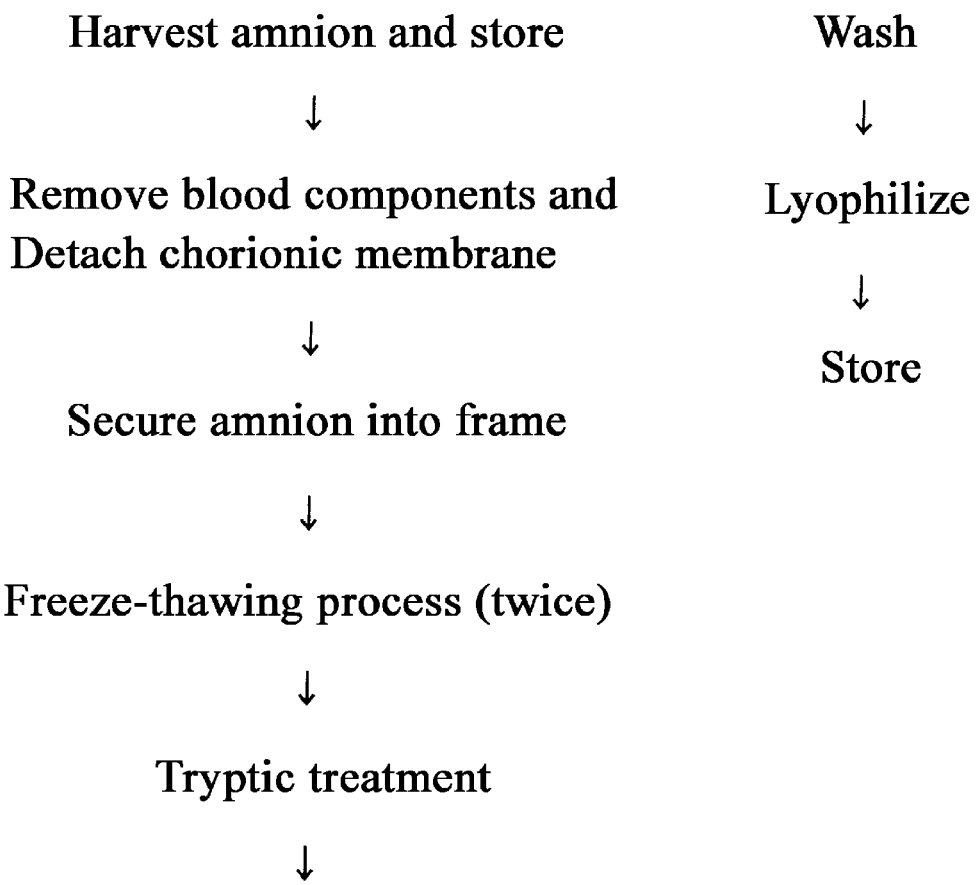
FIG. 15 is a flow chart showing the removal procedure of amniotic epithelium.

Amnion was processed according to the procedure shown in FIG. 15 to prepare amnion with its epithelium removed (non-epithelium-containing amnion). Operation method (processing method), operation condition (processing condition), and other details will now be described.

9-1. Harvesting of Amnion

A sufficient informed consent was obtained in advance from a pregnant woman who had no systemic complications but was undergoing a caesarian operation, in the presence of an obstetrician. An amnion was obtained from the woman during the caesarian operation in operation room. The operation was performed with cleanness being ensured, and with a dedicated garment worn after scrubbing according the surgical procedure. Before delivery, a clean vat for harvesting amnion and physiological saline for washing were prepared. After delivery, placental tissue was transferred to the vat and amniotic tissue was manually detached from the placenta. Any firm adhesion between the amnion and placenta was cut off using a scissor.

9-2. Removal of Blood Components and Detachment of Chorionic Membrane

Blood components attached to the amnion obtained were washed off with physiological saline, and an additional sufficient amount of physiological saline (0.005% ofloxacin added) was used to wash further. Then, chorionic membrane adhered to the amnion was manually removed.

9-3. Securing of Amnion

Amnion was secured according to the method shown in FIG. 2b. First, the amnion was mounted on a sterilized film made of fluorocarbon resin with epithelial side facing upward. The amnion was then spread wide to eliminate any wrinkle and sag, and a sterilized sheet frame made of fluorocarbon resin was mounted on the amnion. Clips or other device was used to secure the sheet of fluorocarbon resin and the sheet frame of fluorocarbon resin, thereby clamping the amnion between the fluorocarbon resin-made sheet and the fluorocarbon resin-made sheet frame (Scuring of frame). An excess portion of the amnion that protruded was cut out. Epithelial side's facing upward was ensured by observation under stereoscopic microscope.

9-4. Freeze-Thawing Process

The amnion secured into a frame was transferred in to a deep freezer at $-80°$ C., and left stood for about 30 minutes (Freezing). The amnion was then taken out from the deep freezer, transferred into an incubator at $37°$ C., and left stood for about 30 minutes (Thawing). The above procedure was performed another time.

9-5. Tryptic Treatment

Following the freeze-thawing process, the amnion was immersed in tryptic solution (0.02% trypsin, 0.2 mM EDTA-containing phosphate buffer solution) with the amniotic epithelial side facing upward, and left stood for about 15 minutes ($37°$ C.). The immersion method was as shown in FIG. 16a. Specifically, amnion 10 secured into a frame was retained, with the fluorocarbon resin-made sheet 4 facing downward, and tryptic solution 5 was added into fluorocarbon resin-made sheet frame 3. This results in immersion of only the epithelial portion of amnion 10 in tryptic solution 5. As shown in FIG. 16b, amnion 10 secured into a frame may be put into container 6 with the epithelial side facing downward, thereby attaining immersion in tryptic solution 5. In the instant example, by engaging protrusions on the inside of container 6 with fluorocarbon resin-made sheet frame 3', a desired relative position between liquid surface 5a of tryptic solution 5 and amnion 10.

9-6. Washing

Following the tryptic treatment, the amnion is removed from the fluorocarbon resin-made sheet and fluorocarbon resin-made sheet frame, transferred into PBS, and washed by shaking therein (140 rpm 15 minutes, twice). This procedure removes tryptic solution and amniotic epithelial cells.

9-7. Lyophilization

The amnion after washing was clamped by a pair of sterilized plastic frames, and secured. Each of the frames was separately transferred into deep freezer at $-80°$ C., and, upon determination of freezing of the amnion, lyophilization process ($-110°$ C., about an hour) was performed using vacuum dryer (Yamato, NEOCOOL). Conditions were set according to the instruction from the manufacturer such that sufficiently desiccated products can be obtained. The amnion after the lyophilization process was released from the plastic frame, transferred into a two-layered bag made of polyamidenylon on the outside and polyethylene on the inside, and packed in vacuum using a vacuum packer for home use (Framenova, Magicpack). The amnion packed in vacuum was irradiated with γ-ray (about 25 kGy) to sterilize it. The sterilized amnion was stored in the vacuum package at a normal temperature until immediately before use. The state immediately after the lyophilization process was still maintained even 12 months after start of the storage.

9-8. Review of Freeze-Thawing Process and Removal Method of Epithelium by Tryptic Treatment The method of removing epithelium as described above was evaluated according to the following procedure. The evaluation experiment used epithelium-non-containing amnion (trypsin-treated amnion) that is obtained by washing the amnion post tryptic treatment.

(1) HE Staining

Epithelium-non-containing amnion (trypsin-treated amnion) was HE stained according to the following method. Amnion which had not undergone epithelium removal (raw amnion) and that with its epithelium manually removed (manually treated amnion) were used as compared subjects.

First, each of epithelium-non-containing amnion (trypsin-treated amnion), raw amnion and amnion with its epithelium manually removed (manually treated amnion) were cut into a size of 1.5×1.5 cm, embedded in OCT compound, and frozen at −80° C. to provide frozen preparations. These preparations in the frozen state were sliced into a thickness of 8 µm in the vertical direction to amniotic surface in cryostat (CM1900 Leica), and mounted on glass slide to provide as frozen section.

Procedures and conditions for the HE staining were as follows. 1.10% formaldehyde solution 5 min., 2. Washing in Running Water, 15 min., 3. Hematoxylin solution, 10 sec., 4. Washing in Running Water, 15 min., 5. Eosin solution, 10 min., 6. Washing in Running Water, 15 min., 7.70% ethanol, 10 sec., 8.90% ethanol, 10 sec., 9. 95% ethanol, 10 sec., 10. 100% ethanol, 10 sec., 11. 100% xylene, 10 sec., 12. 100% xylene, 30 min. and 13. Mounting.

Samples after mounting were visualized under light microscope (Olympus BX50).

If hematoxyn is used for the staining of amnion, the amniotic epithelial cells are stratum compactum nucleated cells are stained. In contrast, if eosin is used for staining, stratum compactum is stained. Thus, through the HE staining, the presence or absence of detachment of epithelial cells, as well as the presence or absence of any damage to stratum compactum can be identified.

Figure 17:
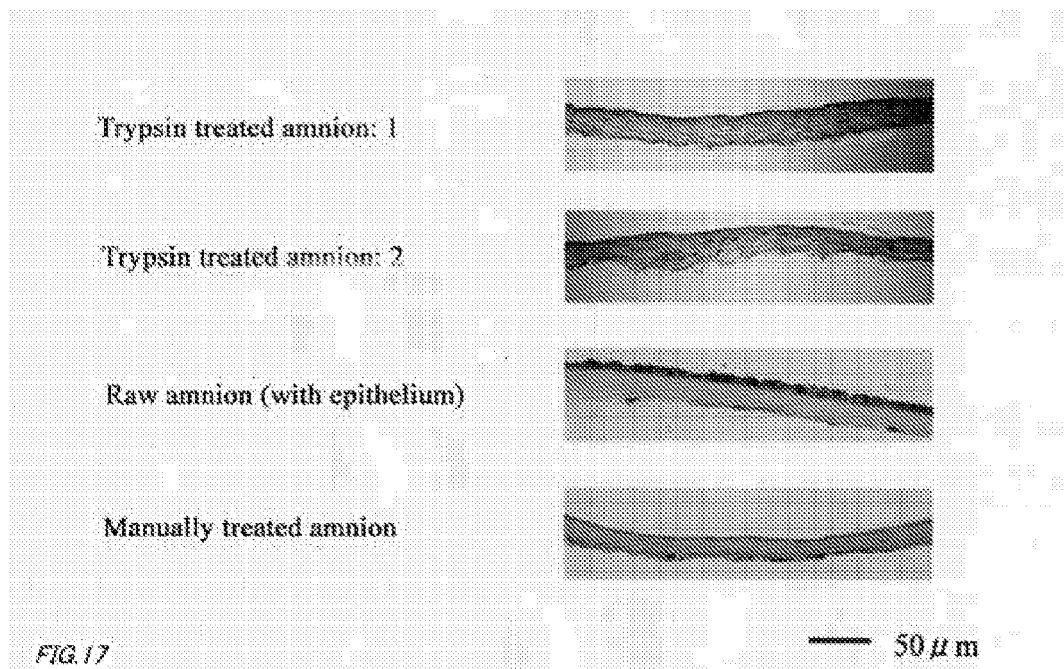
FIG. 17 is a series of photographs showing HE staining images of trypsin-treated, raw (with epithelium attached), and manually-treated amnions.

Results of the HE staining are shown in FIG. 17. Cell layer (epithelium) can be observed in raw amnion. In trypsin-treated amnion, no cell layer (epithelium) can be observed, similarly to manually treated amnion. As a result, it was determined that epithelium can be removed completely and evenly through the above method. Meanwhile, no damage in the stratum compactum was found.

(2) Immuno-staining of Basal Membrane and Stratum Compactum Components

In order for amnion to favorably act as a substrate for cell culture, it is believed that the basal membrane and stratum compactum preferably have retained their innate structures, in addition to the requirement for complete removal of epithelium. Whether or not the basal membrane and stratum compactum have retained their innate structures can be evaluated by examining the presence or absence (whether or not they are retained) of components characteristic of each of these. Thus, the following immuno-staining method was used to examine whether or not the basal membrane and stratum compactum components are retained in trypsin-treated amnion. Similarly to the case of HE staining, amnion which had not undergone epithelium removal (raw amnion) and that with its epithelium manually removed (manually treated amnion) were used as compared subjects. The method for producing the frozen sections of amnion is similar to that of HE staining. Such sections were used for performing the immuno-staining according to the following procedure.

1. Acetone fixation, 5 min., 2. Washing in PBS, 30 min., 3. Blocking with PBS/3% BSA, 15 min., 4. First antibody, 1 hour, 5. Washing in PBS, 30 min., 6. Blocking with PBS/3% BSA, 15 min., 7. Second antibody, 1 hour, 8. Washing in PBS, 30 min. and 9. Mounting.

Samples after mounting were visualized under fluorescence microscope (Leica DMIRB).

Used antibodies were as follows, and dosages were determined according to the instruction from the manufacturer.

Collagen I (Collagen I): LSL LB-1190, Collagen III (Collagen III): LSL LB1300, Collagen IV (Collagen IV): LSL LB-1407, Collagen V (Collagen V): LSL LB1581, Collagen VII (Collagen VII): Chemicon MAB1345, Laminin 5 (Laminin-5): Chemicon MAB19562, Fibronectin (Fibronectin): LSL LB-1021.

Amniotic basal membrane layer has Collagen IV, II and Laminin 5 expressed, while stratum compactum has Collagen I, III, V and Fibronectin expressed. Therefore, immuno-staining using antibodies for each of these allows for visualization of any amniotic basal membrane and stratum compactum that were retained. In addition, since PI staining is also performed in the instant experiment, the presence or absence of amniotic epithelial cells can be simultaneously determined.

Figure 18:
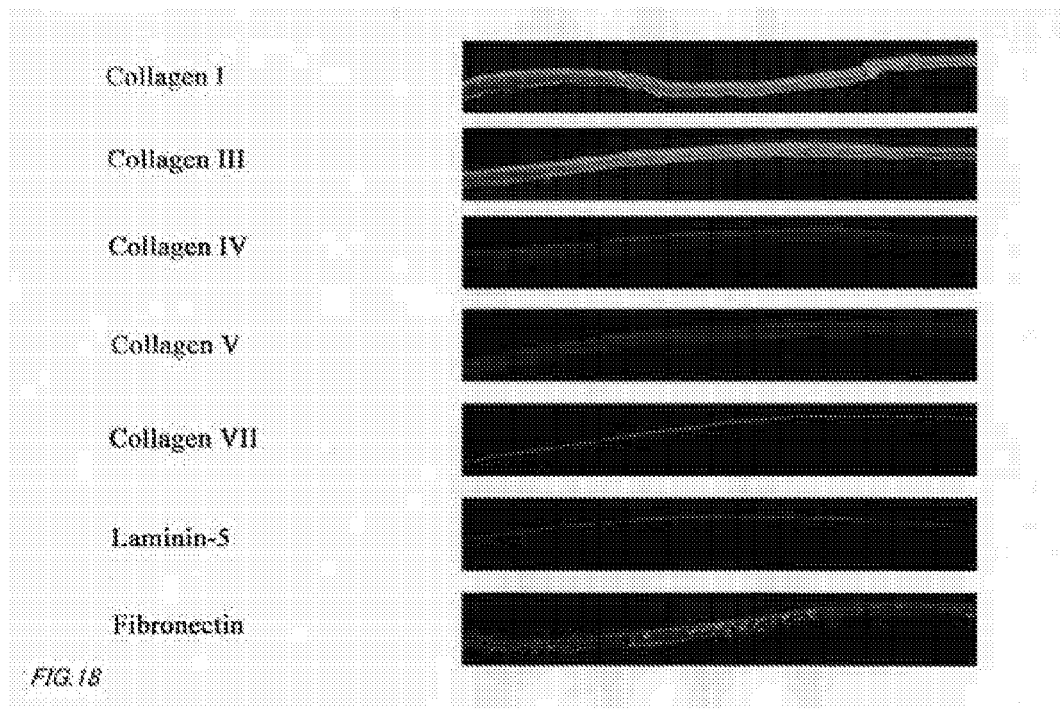
FIG. 18 is a series of photographs showing the immuno-staining images of the trypsin-treated amnion.
Figure 19:
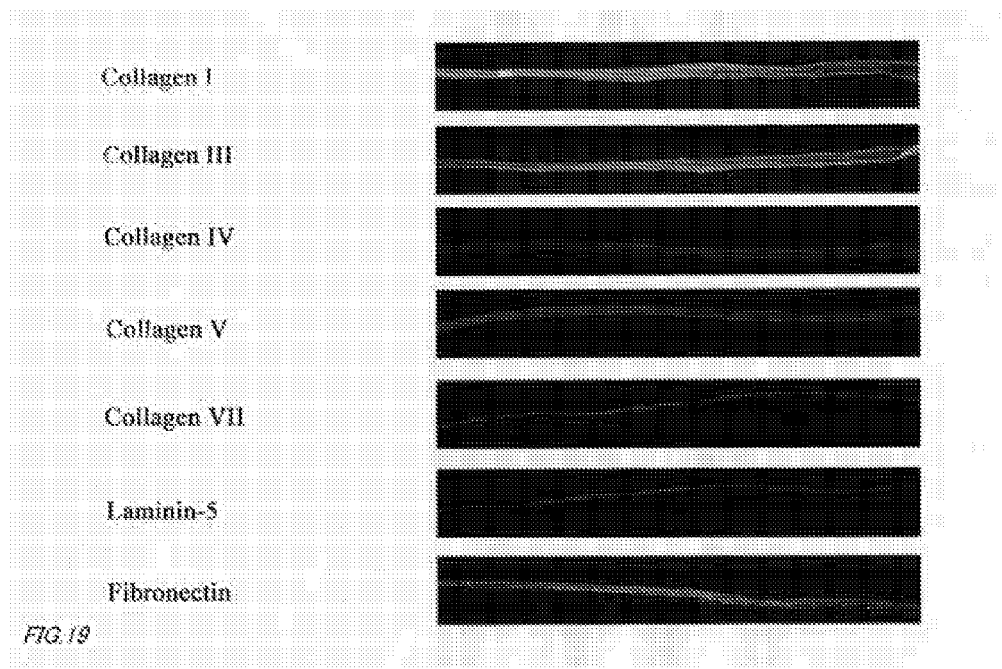
FIG. 19 is a series of photographs showing the immuno-staining images of the trypsin-treated amnion.
Figure 20:
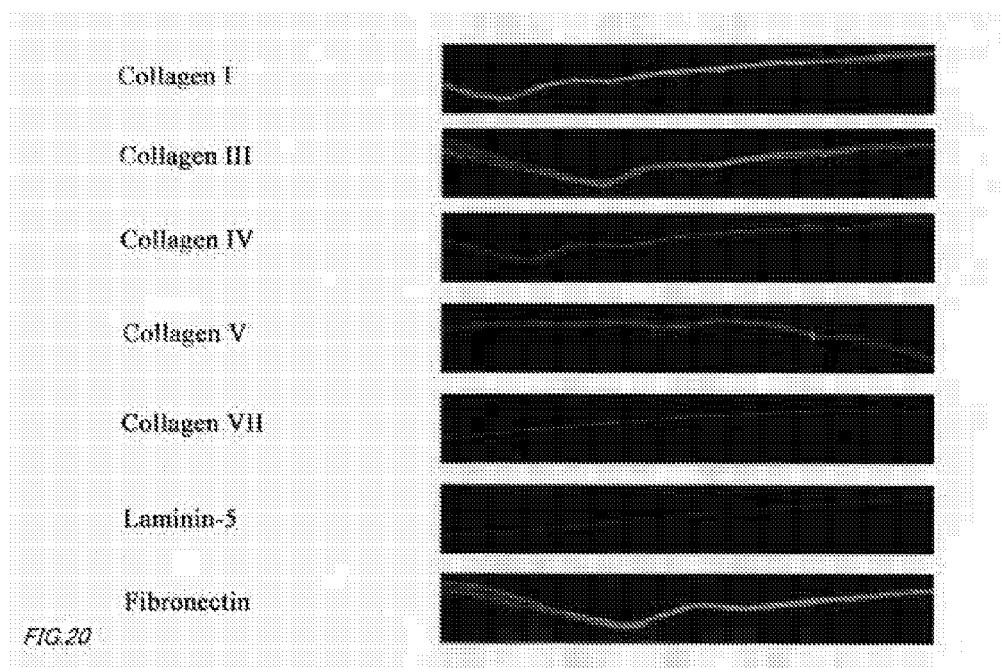
FIG. 20 is a series of photographs showing the immuno-staining images of the raw (with epithelium attached) amnion.
Figures 21, 22:
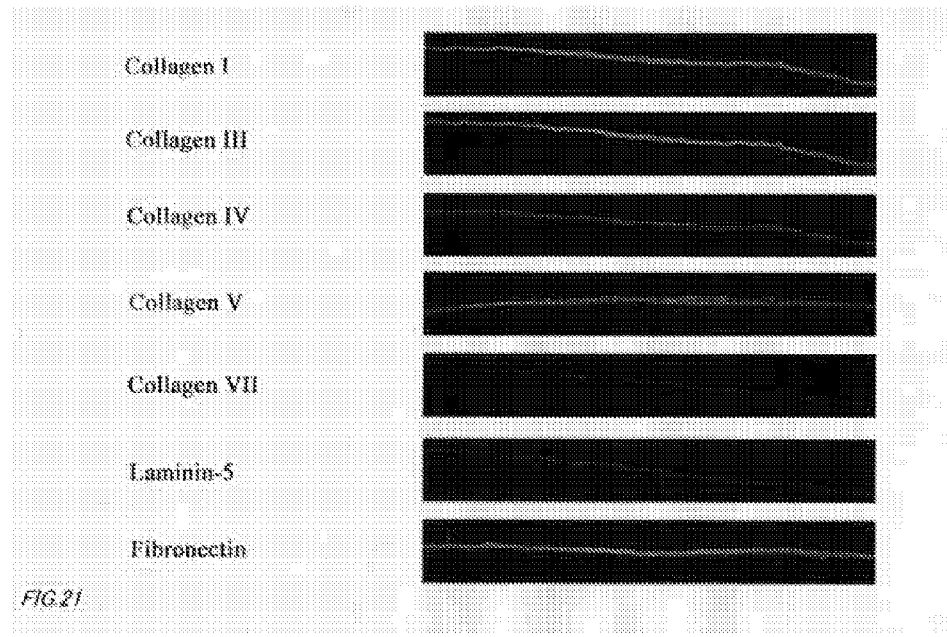
FIG. 21 is a series of photographs showing the immuno-staining images of the manually-treated amnion.
FIG. 22 is a table summarizing the results of HE staining experiment and immuno-staining experiment.

Results of the immuno-staining are shown in FIG. 18 through 21. FIGS. 18 and 19 are immuno-staining images of trypsin-treated amnions, FIG. 20 is an immuno-staining image of raw amnion (with epithelium thereon), and FIG. 21 is an immuno-staining image of manually treated amnion. Summary of the immuno-staining results are shown in FIG. 22. As is apparent from these results, trypsin-treated amnion retains it basal membrane and stratum compactum components to a similar degree to those in manually treated amnion. Specifically, the above treatment method enables to retain the basal membrane and stratum compactum components equivalently to conventional, manual treatment method.

9-9. Summary

It was observed in the above results of experiment that, by processing the amnion with the freeze-thawing and tryptic treatment in combination, epithelium can be completely removed without substantially damaging amniotic basal membrane and stratum compactum (i.e. with a favorable retention of innate structure).

INDUSTRIAL APPLICABILITY

The sheet-shaped according to the invention can be useful in an extensive field, such as transplant material for reconstructing tissues, and antiadhesive material. Exemplary applied fields for the sheet-shaped composition according to the invention are fields of ophthalmology, digestive surgery, gynecology and dermatology.

This invention is not limited in any way by the Mode of Operation and Embodiments described above. The present invention encompasses various modifications that are readily thought of by those who skilled in the art.

Contents of any thesis, Published patent application and Patent Gazette specified in the present specification are hereby incorporated by reference for their entirety.

The invention claimed is:

1. A sheet-shaped composition comprising an amnion having its epithelial cell layer removed, said composition lyophilized and trehalose-treated, wherein said composition has an enhanced tensile strength compared to raw amnion.

2. The sheet-shaped composition according to claim 1 in a frozen or desiccated state.

3. The sheet-shaped composition according to claim 1 wherein said sheet-shaped composition has an increased clarity compared to a sheet-like composition comprising amnion with epithelium removed, lyophilized, which has not been trehalose-treated, and wherein said increased clarity is capable of being evaluated by measuring turbidity, calculated according to the equation: Haze=Diffuse Transmission Factor (DF)/Total Light Transmittance.

4. The sheet-shaped composition according to claim 1, wherein said amnion has basal membrane components Collagen IV, Collagen VII, and Laminin 5 that are detected at an equivalent intensity to that in untreated amnion.

5. The sheet-shaped composition according to claim 1, wherein said amnion is a human amnion.

6. The sheet-shaped composition according to claim 1, wherein a cell layer consisting of tissue-derived cells is formed on said amnion.

7. The sheet-shaped composition according to claim 6, wherein said tissue-derived cells are layered in the cell layer.

8. The sheet-shaped composition according to claim 6, wherein said tissue-derived cells are derived from corneal epithelium, conjunctival epithelium, skin epidermis, follicular epithelium, oral mucosa epithelium, pigment epithelium iris, pigment epithelium retina, airway mucosa epithelium, or intestinal mucosa.

9. The sheet-shaped composition according to claim 6, wherein said cell layer is composed of about 5-7 layered cells, and has properties similar to those of corneal epithelium.

10. The sheet-shaped composition according to claim 1, for use as antiadhesive materials or reconstruction materials for surface of tissues damaged during surgical invasion.

11. The sheet-shaped composition according to claim 1, wherein said amnion has an adhesive component attached on its chorion side surface.

12. The sheet-shaped composition according to claim 11, wherein said adhesive component comprises fibrinogen and thrombin.

13. The sheet-shaped composition according to claim 11, wherein said adhesive component comprises fibrinogen, thrombin and aprotinin.

14. The sheet-shaped composition according to claim 1, wherein the chorion side surface of the amnion is covered with bioabsorbable material.

15. A Transplant method using the sheet-shaped composition according to claim 1 as implant material.

16. A method for producing a sheet-shaped composition, comprising the steps of:
   (a) preparing an amnion having its epithelial cell layer removed; and
   (b) adding trehalose to said amnion;
   (c) freezing or desiccating said amnion.

17. The method according to claim 16, further comprising the step of: (d) sterilizing said amnion after step (c).

18. The method according to claim 16, wherein step (a) comprises the following steps of:
   (i) separating an amnion from an organism,
   (ii) freeze-thawing said amnion,
   (iii) subjecting said amnion after freeze-thawing to tryptic treatment,
   (iv) washing said amnion after tryptic treatment.

19. The method according to claim 18, wherein the freezing temperature during said freeze-thawing process is from about −20° C. to about −80° C., and the thawing temperature is from about 4° C. to about 50° C.

20. The method according to claim 18, characterized by repetition of said freeze-thawing process twice or more times.

21. The method according to claim 18, characterized by the tryptic treatment being performed using a tryptic solution having a tryptic concentration of from about 0.01% (w/v) to about 0.05% (w/v).

22. The method according to claim 21, characterized by the tryptic solution comprising from about 0.1 mM to about 0.6 mM of a chelator selected from the group consisting of EDTA, NTA, DTPA, HEDTA, GLDA, and any combination thereof.

23. The method according to claim 18, characterized by the tryptic treatment being performed under the condition such that the tryptic solution is contacted with only the epithelium side of said amnion.

24. The method according to claim 16, wherein the following step of forming a cell layer consisting of tissue-derived cells on said amnion is performed after step (b).

\* \* \* \* \*